(12) United States Patent
Purushothaman et al.

(10) Patent No.: US 11,257,579 B2
(45) Date of Patent: Feb. 22, 2022

(54) SYSTEMS AND METHODS FOR MANAGING AUTOIMMUNE CONDITIONS, DISORDERS AND DISEASES

(71) Applicant: Progentec Diagnostics, Inc., Oklahoma City, OK (US)

(72) Inventors: Mohan Purushothaman, Oklahoma City, OK (US); Arif Latif Sorathia, Washington, DC (US)

(73) Assignee: Progentec Diagnostics, Inc., Oklahoma City, OK (US)

( * ) Notice: Subject to any disclaimer, the term of this patent is extended or adjusted under 35 U.S.C. 154(b) by 0 days.

(21) Appl. No.: 16/866,498

(22) Filed: May 4, 2020

(65) Prior Publication Data

US 2021/0343384 A1 Nov. 4, 2021

(51) Int. Cl.

| G16H 20/10 | (2018.01) |
| G16H 10/60 | (2018.01) |
| G16H 15/00 | (2018.01) |
| G06N 3/08 | (2006.01) |
| G16H 80/00 | (2018.01) |
| G16B 40/20 | (2019.01) |
| G16H 50/20 | (2018.01) |

(52) U.S. Cl.
CPC .............. *G16H 20/10* (2018.01); *G06N 3/08* (2013.01); *G16B 40/20* (2019.02); *G16H 10/60* (2018.01); *G16H 15/00* (2018.01); *G16H 50/20* (2018.01); *G16H 80/00* (2018.01)

(58) Field of Classification Search
CPC ........ G16H 20/10; G16H 10/60; G16H 15/00; G16H 50/20; G16H 80/00; G16B 40/20; G06N 3/08
See application file for complete search history.

(56) References Cited

U.S. PATENT DOCUMENTS

| 2014/0161769 | A1* | 6/2014 | Tsokos ................... A61K 31/00 424/85.4 |
| 2016/0259899 | A1 | 9/2016 | Ludviksson et al. |
| 2017/0004260 | A1* | 1/2017 | Moturu ................. G16H 50/20 |
| 2019/0108912 | A1* | 4/2019 | Spurlock, III ......... G16B 40/20 |
| 2019/0385752 | A1* | 12/2019 | Bowland ............... G16H 10/60 |

FOREIGN PATENT DOCUMENTS

WO 2019055879 A2 3/2019

\* cited by examiner

*Primary Examiner* — Michael Tomaszewski
*Assistant Examiner* — Jay M. Patel
(74) *Attorney, Agent, or Firm* — Gregory Finch; Finch Paolino, LLC

(57) ABSTRACT

An artificial intelligence (AI) system and methods for management of an autoimmune or inflammatory condition, disorder or disease in a patient for the diagnosis, prognosis, or risk assessment of symptoms thereof. The AI system includes patient and provider applications and a payer application interface accessible via a communications network. The system contains a data-driven recommendation engine using machine learning and/or deep learning based on active monitoring of patients with an autoimmune or inflammatory-related condition, disorder, or disease. The system can alert clinicians to an impending symptom flare and provide a treatment solution that reduces symptom severity, reduces or eliminates the onset.

19 Claims, 16 Drawing Sheets

SYSTEMS AND METHODS FOR MANAGING AUTOIMMUNE CONDITIONS, DISORDERS AND DISEASES

FIELD

The present disclosure relates to the field of digital data processing systems and corresponding data processing methods and products for emulation of intelligence, machine learning systems, and artificial neural networks. In particular, provided are artificial systems and methods for aggregating and analyzing healthcare data to generate diagnostic measures, predictive analytics, and recommendations relating to the management of autoimmune or inflammatory-related conditions, disorders, and diseases.

BACKGROUND

Autoimmune diseases are immune system diseases characterized by the production of antibodies directed against the self (i.e., autoantibodies), which react with the subject's own antigens. Depending on the involved mechanisms of action, certain autoimmune diseases have at times also been classified as inflammatory diseases. Some of the most common autoimmune and/or inflammatory diseases include: Lupus erythematosus, uveitis, Behcet's disease, sarcoidosis, Sjogren's syndrome, rheumatoid polyarthritis, juvenile polyarthritis, Fiessinger-Leroy-Reiter syndrome, gout, osteoarthritis, polymyositis, myocarditis, primary biliary cirrhosis, Crohn's disease, ulcerative colitis, multiple sclerosis and other demyelinating diseases, aplastic anemia, idiopathic thrombocytopenic purpura, any disease associated with non-tumor lymphoproliferation, B-cell lymphoma, Simmonds' panhypopituitarism, Basedow-Graves' disease and Graves' ophthalmopathy, subacute thyroiditis and Hashimoto's disease, Addison's disease, chronic hepatitis, and Type I Diabetes Mellitus.

As merely one example of a highly relevant autoimmune disease—Lupus erythematosus (Lupus) is a chronic systemic autoimmune disease in the family of connective tissue diseases, typically involving many organs and showing significant variations in expression among patients. Variations of Lupus include cutaneous lupus erythematosus (CLE), disseminated lupus erythematosus (DLE), and systemic lupus erythematosus (SLE). CLE is a particularly polymorphic affliction traditionally divided into three groups: chronic CLE, which includes discoid lupus, tumid lupus, lupus pernio and lupus profundus (or panniculitis); subacute CLE (SCLE), and acute CLE (ACLE). Dermatological manifestations observed during SLE, which can be used for schematic classifications, include, e.g., lupus lesions (histology being suggestive of lupus) and vascular lesions (cutaneous vasculitis). The autoimmune or "anti-self" response in SLE patients in particular is characterized by proliferation of autoantibodies directed against a variety of nuclear and cytoplasmic cellular components. Upon binding to their respective antigens, the autoantibodies form immune complexes that circulate and eventually deposit in tissues, resulting in chronic inflammation and tissue damage.

The spectrum of Lupus in patients is broad and can range from subtle or vague symptoms to life-threatening, multi-organ failure. Various other diseases that involve multi-organ failure can also be mistaken for Lupus, and vice versa. Therefore, the accurate diagnosis of Lupus can be problematic in some patients. Additionally, because Lupus typically progresses in a series of flares, or periods of acute illness, followed by remissions, the monitoring of disease progression in patients with Lupus can also be problematic. The flare symptoms vary considerably between patients and even in the same patient, and can include malaise, fever, symmetric joint pain, and photosensitivity (development of rashes after brief sun exposure). Because the typical flares often occur between regularly scheduled healthcare visits, they may go unreported or be inaccurately described by the patient at the time of the scheduled visit. Therefore, given the subjective nature, subjective recognition, episodic occurrences, and onset unpredictability of flares, lupus is particularly difficult to monitor and manage.

Deep Learning (DL) is a new form of machine learning (ML) that has dramatically improved the performance of machine learning tasks. DL uses artificial neural networks (ANNs) that apply layers of interconnected linear or non-linear mathematical transformations to data in order to solve a problem, such as signal or object recognition, classification, and segmentation. The level of DL performance is greater than in classical ML and ideally does not require a human to identify and compute the critical features. Instead, during training, DL algorithms "learn" discriminatory features that best predict the outcomes. Therefore, less human effort is typically required to train DL systems than to train ML systems due to the necessary engineering and computations involved.

The superiority of computer assisted diagnostic decision making based on DL has recently been reported for a wide spectrum of diseases, including gastric cancer, diabetic retinopathy, cardiac arrhythmia, skin cancer, and colorectal polyp. These studies were based on a wide variety of diagnostic modalities, including, e.g., pathological slides, electrocardiograms, and radiological images. To date, however, an effective system for feature extraction, or phenotyping, of Lupus patients and their symptoms for predicting potential flares has not been achieved.

Digital phenotyping refers to the moment-by-moment quantification of the individual-level human phenotype in situ using data from personal digital devices to develop illness signatures that can inform treatment decisions. The ubiquitous access to digital technologies worldwide has enabled new opportunities to examine individuals' health behavior and conditions through intensive data collection using mobile devices, wearable sensors, continuous monitoring, and mapping digital footprints. A variety of computer-readable data can be used to differentiate or to quantify phenotypes, ranging from passive, unobtrusive monitoring via sensors to active patient-reported (questionnaire data) outcomes with smartphones. Smartphones offer the ability to collect both active and passive data.

Active data, similar to ecological momentary assessment using prompts for subjects to report on their current symptoms, reflects the user's engagement (e.g., taking a survey) and is generated by the user's choice or active participation. Passive data, on the other hand, can be collected without user engagement, and may include, e.g., sensor measurements (built-in global positioning systems (GPS) and accelerometers), inertial measurements, as well as phone usage, such as call logs, text logs, and screen activity. The origin of digital phenotyping stems from its exploratory use in mental health applications such as for the prediction of relapses in patients with schizophrenia. Digital phenotyping has the potential to quantify Lupus patient's daily activities and external factors that may provide insights into the onset and occurrences of symptoms and enable personalized interventions facilitated by healthcare providers. However, the lack of features or digital flare phenotypes has complicated the development of a platform that would enable the optimal management of patients with Lupus and other autoimmune or inflammatory-related conditions, disorders, and diseases.

There exists a need for a system of aggregating and analyzing healthcare data from a variety of sources and generating clinically validated diagnostic measures and predictive analytics for the management of symptoms, therapies, and interventions of autoimmune and inflammatory conditions, disorders, and diseases. Through applied effort, ingenuity, and innovation, applicant has identified deficiencies of prior art solutions and has developed a solution that is embodied by the present disclosure, which is described in detail below.

SUMMARY

In order to provide a basic understanding of the invention, the following is a simplified summary of certain embodiments thereof. This summary is not extensive and is not intended to identify key/critical elements of the invention or to delineate the scope of the invention. Its sole purpose is to present embodiments of the invention in a simplified form as a prelude to the more detailed description that is further below.

As used herein, an "aiSLE" platform, engine, and/or application comprises one or more of artificial intelligence systems, methods, apparatuses, and computer readable mediums for the clinical management of autoimmune or inflammatory conditions, disorders, and diseases.

In general embodiments of the invention, provided is an artificial intelligence system comprising an engine or platform that aggregates and analyzes healthcare data from a variety of sources and generates clinically validated diagnostic measures and recommendations to healthcare providers. The platform comprises at least one healthcare provider application (or "providerApp") and a patient application ("patientApp") communicably connected for the clinical management of patients. In certain embodiments, the engine aggregates data from the at least one healthcare "providerAPP", "patientAPP" (including, but not limited to, wearable device data), a Lab Information Management System (LIMS), and an electronic medical record (EMR). The engine further analyzes the aggregate data using machine learning models, including, but not limited to, at least one artificial neural network, a deep learning neural network, or the like, to create diagnostic measures and/or predictions and recommendations for a healthcare provider, clinician, or digital health coach.

In embodiments, the artificial intelligence system comprises one or more interfaces for a patient, a healthcare provider, and/or a payer, at least one engine application program interface (API), an engine, a mobile back end, and a data store residing on at least one cloud server. Additionally, the platform may comprise one or more external sources of data generation and/or storage medium, including, but not limited to, EMR, external API, LIMS, and the like.

Specifically, provided in various embodiments of the invention is a system for predictive screening or management of an autoimmune or inflammatory-related condition, disorder, or disease, comprising: a mobile electronic device configure to execute an instance of a graphical user interface comprising a plurality of user prompts associated with an autoimmune or inflammatory-related condition, disorder, or disease of a patient user; an integral or remote processor communicatively engaged with the mobile electronic device; and a non-transitory computer readable medium having instructions stored thereon that, when executed, cause the processors to perform one or more operations, the one or more operations comprising operations for: receiving a plurality of user-generated inputs in response to the plurality of user prompts; receiving one or more sensor inputs comprising a patient activity input or a patient physiological input; receiving one or more external data inputs comprising at least one patient historical data input; aggregating the plurality of user-generated inputs, the one or more sensor inputs, and the one or more external data inputs to define an aggregated dataset; analyzing the aggregated dataset according to at least one machine learning framework comprising at least one supervised learning model or artificial neural network, wherein the at least one machine learning framework comprises at least one dependent variable corresponding to a current or future state of the autoimmune condition; generating at least one diagnostic measure of the current or future state of the autoimmune condition according to the at least one machine learning framework; and generating, with the processor, at least one activity recommendation in response to the at least one diagnostic measure, the at least one activity recommendation corresponding to at least one patient action associated with the current or future state of the autoimmune or inflammatory-related condition, disorder, or disease. In embodiments, the system further comprises at least one wearable electronic device communicatively engaged with the process, the at least one wearable electronic device comprising at least one sensor configured to receive the patient activity input or the patient physiological input.

In certain embodiments, the plurality of user-generated inputs comprises one or more patient-reported outcomes in response to the at least one activity recommendation. For example, the at least one activity recommendation may be a recommended laboratory diagnostic procedure that comprises an antibody test. In embodiments, the at least one activity recommendation comprises at least one of a recommended pharmacological intervention, a recommended non-pharmacological intervention, and a laboratory diagnostic procedure. The one or more data inputs may comprise at least one environmental condition corresponding to a location of the patient user, the at least one environmental condition comprising a UV index.

According to embodiments of the invention, a provider can make clinical decisions based on an analysis from the platform using the providerAPP. The providerAPP is configured to enable a provider to access the platform or engine and to prescribe a solution to a patient. In further embodiments, a provider can use the providerAPP to select at least one product selected from the group consisting of a diagnostic, intervention, prescription, recommendation, and prophylactic relating to an autoimmune or inflammatory condition, disorder, or disease. In certain embodiments, the providerAPP is configured to also enable/allow a provider to view or receive results of a diagnostic measure, a prediction, and/or recommendations stored within at least one EMR.

According to embodiments of the invention, the patientAPP is configured to enable a patient suffering from an autoimmune or inflammatory-related condition, disorder, or disease to collect and/or record medications, symptoms, adverse effects, adverse events, or other patient-reported outcomes. In certain embodiments, the patientAPP is be configured into a digital technology device that is operable with said patientAPP and wearable by the patient, such as a portable computing device. A portable computing device according to embodiments of the invention may comprise a global position system (GPS) configured to capture and track location and/or environmental data relating to the user of the application. In certain embodiments, the portable computing device comprises one or more sensor of at least one selected from the group consisting of inertial measurement units (IMU), light, sound, and touch, the one or more sensor being configured to capture and track a digital signal, signature, and/or derived digital phenotype relating to the user. In embodiments, the patientAPP is configured to enable a user to access one or more wearable devices through the patientAPP to collect data on user activity, heartrate, sleep pattern, weight, body mass, blood pressure, exercise, and the like. In still further embodiments, the patientAPP is configured to enable a patient user to send messages or conduct a live video conference via the application with, e.g., a digital health coach or a health care provider. Message data or notes from the digital health coach may be automatically captured by the patientAPP and processed by the engine. The patientAPP is preferably configured so as to enable the recording of one or more digital phenotypes of a patient user, the processing and analysis of data from one or more digital technology device by the engine, and the sending of one or more recommendations to the patient using the platform or engine.

Certain aspects of the present disclosure provide for one or more API that comprises a dashboard configured to enable a payor to access the engine and track one or more patient and/or health care provider metrics or patient population metrics. The engine may be configured to aggregate data from a data warehouse, a digital app, a patientAPP and/or a providerAPP as described herein, laboratory results, a wearable device, or EMR. In embodiments, one or more artificial intelligence algorithms are utilized to analyze data and to generate one or more reports or insights for at least one of a patient, a provider, or a payor. In still further embodiments, the one or more artificial intelligence algorithms are configured to analyze data and to derive one or more digital phenotypes, a diagnosis, or a prediction relating to the autoimmune or inflammatory symptom, condition, or disease of the patient.

According to further aspects of the invention, data architecture of the system comprises one or more internal and/or external data sources. In certain embodiments, the internal data source comprises mobile computing device data, LIMS data, laboratory data, point of care diagnostic data, and the like. The external data source, on the other hand, may comprise EMR, claims data, and the like. In still further embodiments, the data architecture comprises a data store or warehouse that comprises one or more service such as real-time messaging, batch process controlling, Universally Unique Identifiers (UUID)/patient matching, data transformation, and the like.

According to still further aspects of the invention, provided is a method for the creation of an artificial intelligence model and deployment thereof. In embodiments, the method comprises identifying at least one primary endpoint or dependent variable, creating a model dataset, developing a model, deploying the model, and monitoring the model. In certain embodiments, the method comprises identifying one or more input variables, creating aggregated or calculated variables, cleaning the data, compiling the data, separating the data for development or validation, applying one or more machine learning models to the data, validating the model(s), and creating the final model.

In embodiments, methods of the invention further comprise one or more sub-routines selected from the group consisting of evaluating data quality, creating aggregated or calculated variables, engineering of one or more features, and creating an analytical record. The analytically created record captures one or more features or digital phenotypes relating to an autoimmune symptom, diagnostic, or prognostic measure. The method enables a patient user, a provider and payor to exchange messages, videos, and consultations relating to symptoms, diagnoses, prognoses, intervention, treatment, recommendation, or therapy relating on an autoimmune or inflammatory disease or condition. In embodiments, the model may be implemented by one or more module, such as a measure module, a risk module, a recommendation module, and the like.

Certain aspects of the present disclosure may be embodied as a system, engine, application, app, patientAPP, providerAPP, payer API, wearable, mobile computing device, smartphone, web application, or the like. A platform may be accessible via the Internet, a wireless communication channel, web application, or the like. In embodiments of the invention, the product comprises a hardware implementation or software instructions stored and executable from one or more non-transitory storage medium located locally or remotely on a cloud server or cloud service. In various embodiments, the product is a practical application of one or more machine learning or artificial intelligence network. In preferred embodiments, the artificial intelligence network comprises at least one artificial neural network (ANN), Convolution Neural Network (CNN), Recurrent Neural Network (RNN), Fully Convolutional Neural Network (FCN), Dilated Residual Network (DRN), Generative Adversarial Networks (GANs) architecture, Deep Neural Network (DNN), or the like.

Certain aspects of the present disclosure may comprise an analytical framework incorporating one or more inputs, convolution, pooling, map, sampling, linear, or rectification (non-linear activation function), normalization, full connection (FC), or output layer. The product is configured to enable a user selected from a patient, provider, and payor to manage an autoimmune or inflammatory condition, disorder, or disease of a patient. Specifically, based on active monitoring of a lupus patient, the product described herein generates data-driven recommendations that can assist clinicians in determining the most optimal treatment faster, improving outcomes and reducing organ damage in patients resulting from autoimmunity or inflammation. In embodiments, the product can alert clinicians or providers of an impending patient flare or inflammatory-associated symptoms and provide a treatment recommendation or solution that reduces severity or eliminates onset.

Certain illustrative embodiments of the present disclosure provide for a computer-implemented method for evaluation or management of an autoimmune or inflammatory-related condition, disorder, or disease, comprising: receiving, with a mobile electronic device, a first plurality of data comprising one or more user-generated inputs corresponding to an autoimmune condition of a patient user; receiving, with the mobile electronic device, a second plurality of data comprising at least one environmental condition corresponding to a location of the patient user; receiving, with the mobile electronic device, a third plurality of data comprising at least one physiological measurement associated with the patient user; receiving, with a processor being communicably engaged with the mobile electronic device, the first plurality of data, the second plurality of data, and the third plurality of data; aggregating, with the processor, the first plurality of data, the second plurality of data, and the third plurality of data to define an aggregated dataset; analyzing, with the processor, the aggregated dataset according to at least one machine learning framework comprising at least one supervised learning model or artificial neural network, wherein the at least one machine learning framework comprises at least one dependent variable corresponding to a current or future state of the autoimmune condition; generating, with the processor, at least one diagnostic measure of the current or future state of the autoimmune condition according to the at least one machine learning framework; and generating, with the processor, at least one activity recommendation in response to the at least one diagnostic measure, the at least one activity recommendation corresponding to at least one patient outcome associated with the current or future state of the autoimmune condition.

The computer-implemented method for evaluation or management of an autoimmune or inflammatory-related condition, disorder or disease according to embodiments of the invention may further comprise providing, with the processor, the at least one diagnostic measure and the at least one activity recommendation to a health care provider user. In certain embodiments, the method comprises receiving, with the mobile electronic device, a fourth plurality of data comprising one or more user-generated inputs corresponding to at least one patient-reported outcome in response to the at least one activity recommendation. In certain embodiments, the method further comprises analyzing, with the processor, the at least one patient-reported outcome to determine a measure of efficacy of the at least one activity recommendation. In embodiments, the activity recommendation comprises a pharmacological intervention recommendation comprising a recommended dosage and timing for administering at least one drug selected from the group consisting of a nonsteroidal anti-inflammatory drug, an immunosuppressive drug, and a steroid. In certain embodiments, the activity recommendation comprises a recommended non-pharmacological intervention comprising a recommended UV exposure mitigation action or recommended activity modification.

In embodiments, the method further comprises providing, with the processor, the at least one diagnostic measure, the at least one activity recommendation, and the at least one patient-reported outcome to a health care provider user. In certain embodiments, the at least one activity recommendation may include a recommended laboratory diagnostic procedure comprising an antibody test. In embodiments, the physiological measurement comprises a sensor input from a wearable electronic device.

Further illustrative embodiments of the present disclosure provide for a system for predictive screening or management of an autoimmune condition, the system comprising a mobile electronic device configured to execute an instance of a graphical user interface comprising a plurality of user prompts associated with an autoimmune condition of a patient user; an integral or remote processor communicatively engaged with the mobile electronic device; and a non-transitory computer readable medium having instructions stored thereon that, when executed, cause the processor to perform one or more operations, the one or more operations comprising operations for: receiving a plurality of user-generated inputs in response to the plurality of user prompts; receiving one or more sensor inputs comprising a patient activity input or a patient physiological input; receiving one or more external data inputs comprising at least one patient historical data input; aggregating the plurality of user-generated inputs, the one or more sensor inputs, and the one or more external data inputs to define an aggregated dataset; analyzing the aggregated dataset according to at least one machine learning framework comprising at least one supervised learning model or artificial neural network, wherein the at least one machine learning framework comprises at least one dependent variable corresponding to a current or future state of the autoimmune condition; generating at least one diagnostic measure of the current or future state of the autoimmune condition according to the at least one machine learning framework; and generating, with the processor, at least one activity recommendation in response to the at least one diagnostic measure, the at least one activity recommendation corresponding to at least one patient action associated with the current or future state of the autoimmune condition.

Certain embodiments of the system for predictive screening or management of an autoimmune condition may further comprise at least one wearable electronic device being communicatively engaged with the processor, the at least one wearable electronic device comprising at least one sensor being configured to receive the patient activity input or the patient physiological input.

In embodiments, the plurality of user-generated inputs comprises one or more patient-reported outcomes in response to the at least one activity recommendation. The external data inputs may comprise at least one environmental condition corresponding to a location of the patient user and/or an environmental condition comprising a UV index. The at least one patient historical data input may comprise electronic medical record data or laboratory diagnostic data.

In embodiments, the one or more operations of the method of the invention comprise operations for analyzing the aggregated dataset to generate one or more patient outcome metrics associated with the autoimmune condition of the patient user, providing a communications interface between the mobile electronic device and a provider client device or a health coach client device, and/or communicating the one or more patient outcome metrics to a payor user.

The at least one activity recommendation according to embodiments of the invention comprises at least one of a recommended pharmacological intervention, a recommended non-pharmacological intervention, and a laboratory diagnostic procedure.

Still further embodiments of the present disclosure provide for a non-transitory computer-readable medium encoded with instructions for commanding one or more processors to execute operations of a method for predictive screening or management of an autoimmune condition, the operations comprising one or more operations for: receiving a plurality of data from one or more data sources, the plurality of data comprising one or more user-generated inputs corresponding to an autoimmune condition in a patient user; aggregating the plurality of data to define an aggregated dataset; analyzing the aggregated dataset according to at least one machine learning framework comprising at least one supervised learning model or artificial neural network, wherein the at least one machine learning framework comprises at least one dependent variable corresponding to a current or future state of the autoimmune condition; generating at least one diagnostic measure of the autoimmune condition according to the at least one machine learning framework; and generating at least one activity recommendation in response to the at least one diagnostic measure, the at least one activity recommendation corresponding to at least one patient outcome associated with the autoimmune condition.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be recognized by those skilled in the art that such equivalent structures do not depart from the spirit and scope of the invention.

BRIEF DESCRIPTION OF DRAWINGS

The above and other objects, features and advantages of the present disclosure will be more apparent from the following detailed description of, and in conjunction with, the accompanying drawings, which are briefly described below.

DETAILED DESCRIPTION

Figure 1:
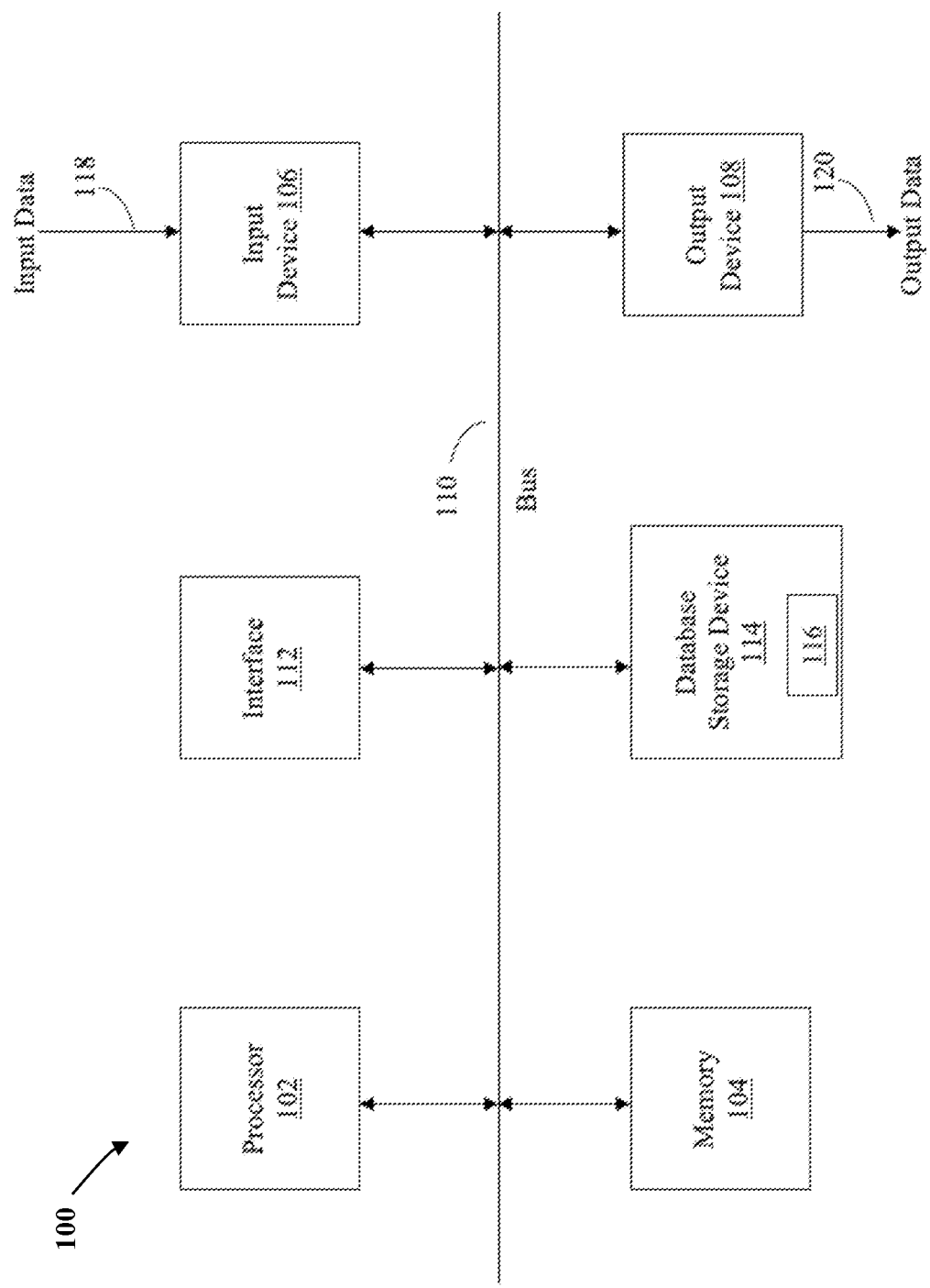
FIG. 1 is an illustrative flow diagram of a computing architecture according to which one or more aspects of the invention may be implemented.

Exemplary embodiments are described herein so as to provide a more detailed description of the invention. Variations of the various embodiments will be apparent to those of skill in the art. Therefore, before specific exemplary embodiments of the invention are described, it is to be understood that this invention is not limited to the exemplified embodiments described herein. It is also to be understood that the terminology used herein is for the purpose of describing certain specific embodiments and is not intended to limit the scope of the invention which is defined only by the appended claims.

Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology. Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

As will be appreciated by one of skill in the art, embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

All definitions, as defined and used herein, should be understood to control over dictionary definitions, definitions in documents incorporated by reference, and/or ordinary meanings of the defined terms. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

As used herein, an "aiSLE" platform, engine, and/or application comprises one or more of artificial intelligence systems, methods, apparatuses, and computer readable mediums for the clinical management of autoimmune or inflammatory conditions, disorders, and diseases.

Embodiments of the present disclosure provide for an artificial intelligence (AI) system and methods for predictive diagnoses, prognoses, and risk assessment in the management of one or more autoimmune or inflammatory condition, disorder or disease symptom(s) (e.g. flares). The AI platform comprises one or more patient and provider application(s) and a payer application program interface accessible via a communications network. The platform contains a data-driven recommendation engine using machine learning and/or deep learning based on active monitoring of patients with an autoimmune or inflammatory condition, disorder, or disease, using a mobile computing device and laboratory diagnostic data that can help clinicians decide on the best treatment faster, improving outcomes and reducing long term organ damage. The system can alert clinicians to an impending symptom flare and provide a treatment solution that reduces symptom severity, reduces or eliminates the onset.

Turning now to the drawings, FIG. 1 depicts an exemplary computing system according to which certain illustrated embodiments of the present invention can be implemented. The processing system 100 generally comprises at least one processor 102, a memory 104, an input device 106 for receiving input data 118 and an output device 108 that produces output data 120 coupled together with at least one bus 110. In certain embodiments, input device 106 and output device 108 could be the same device. An interface 112 can also be provided for coupling the processing system 100 to one or more peripheral devices, for example interface 112 could be a PCI card or PC card. At least one database storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which various embodiments of the invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments of the present invention can be implemented with numerous other general-purpose or special-purpose computing devices, systems or configurations. Examples of well-known computing systems, environments, and configurations suitable for use in embodiment of the invention include, personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Various embodiments of the invention will be described herein in a general context of computer-executable instructions, such as program modules, being executed by a computer. Generally, program modules include routines, programs, objects, components, data structures, etc., that perform particular tasks or implement particular abstract data types. In certain embodiments, distributed computing environments where tasks are performed by remote processing devices that are linked through a communications network may also be employed. In distributed computing environments, program modules may be located in both local and remote computer storage media including memory storage devices.

With the general computing system environment 100 of FIG. 1 being shown and discussed above, the following description and remaining figures pertain to various exemplified embodiments of the present invention generally relating to methods for evaluation or management of an autoimmune disease or condition. In general, the methods described herein involve receiving and aggregating a plurality of patient data from one or more data sources; analyzing an aggregated dataset from the plurality of patient data according to at least one machine learning framework; generating at least one diagnostic measure of a current or future state of an autoimmune or inflammatory condition, disorder, or disease according to the at least one machine learning framework; and generating at least one activity recommendation in response to the at least one diagnostic measure.

Figure 2:
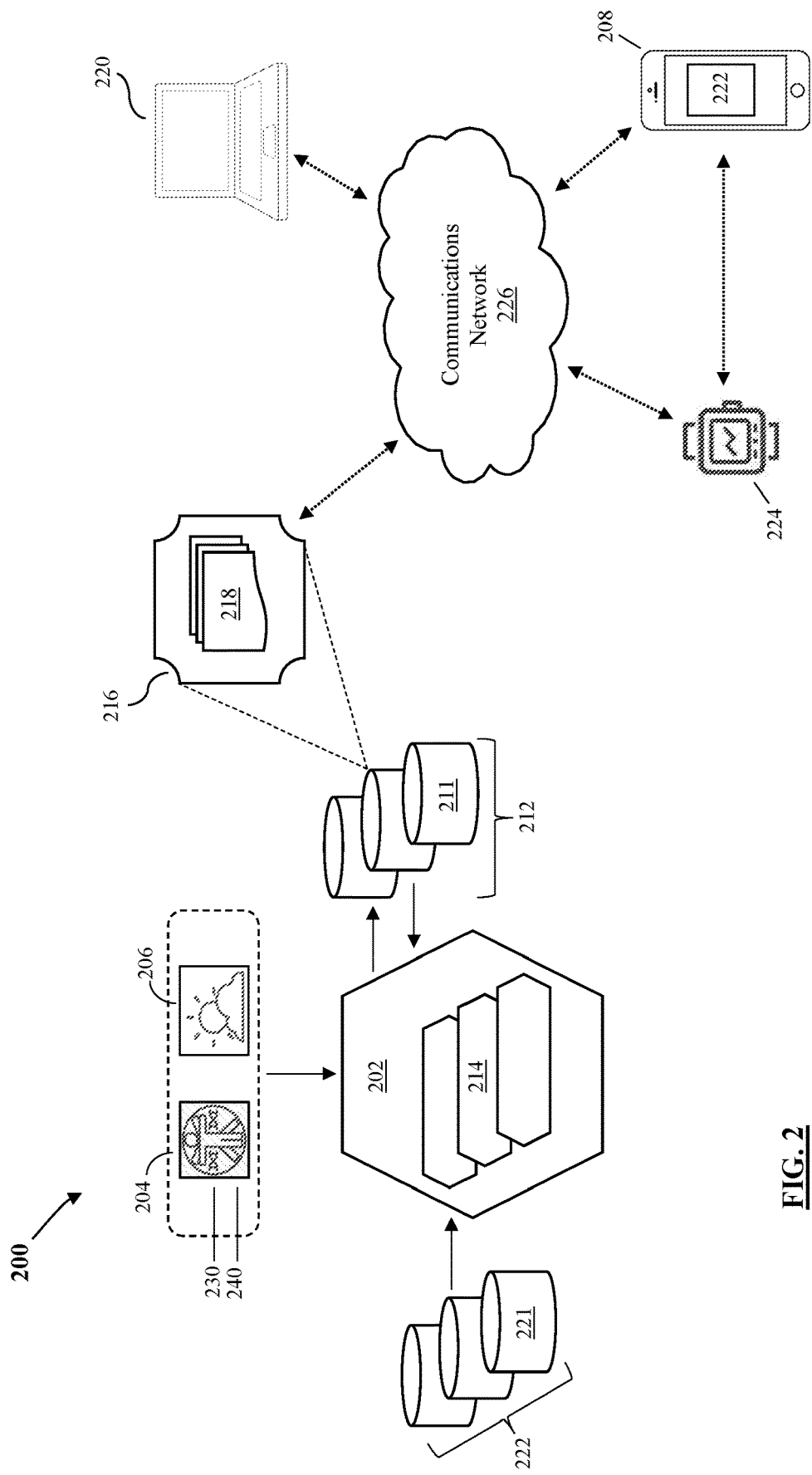
FIG. 2 is a functional diagram of a system according to embodiments of the invention.

Turning now to FIG. 2, provided is a functional diagram of a system 200 according to embodiments of the invention. The system 200 comprises an artificial intelligence (A.I.) engine 202 that receives one or more inputs from at least one of an external database 222 and a cloud-based server 212. In embodiments, the one or more inputs from the external database 222 includes External Medical Record (EMR) data 221, and the one or more inputs from the at least one cloud-based server includes outcome data from an outcome database 211 stored on the at least one cloud-based server 212. In embodiments, the artificial intelligence engine 202 of the system 200 is configured to receive various types of data from one or more additional data sources, such as from a Laboratory Information Management System (LIMS) 204 and an environmental monitoring system 206.

LIMS 204 data may include data relating to diagnostic tests, diagnostic test results, biomarkers, genomic marker, proteomic marker, body fluid analytes, chem panels, metabolites, therapeutic drug levels, and the like. In certain embodiments, LIMS 204 data comprises qualitative and/or quantitative diagnostic results generated or retrieved from a laboratory analyzer 230 and/or a point of care self-test device 240. Environmental data from an environmental monitoring system 206 may include data/measures representative of at least one external condition selected from the group consisting of (UV) radiation, sunlight level, pollen count, ecological information, location or GPS data, and environmental inputs.

As indicated above and shown in FIG. 2, an artificial intelligence engine 202 of the system 200 is configured to receive inputs from at least one external database 222 and at least one outcome database 211/cloud-based server 212. An EMR database 221 may comprise medical records of a patient suffering from or at risk for, an autoimmune or inflammatory condition, disorder, or disease. In certain embodiments, the autoimmune or inflammatory condition, disorder, or disease of the patient is lupus. Similarly, the outcome database 211 may comprise records and data relating to treatment, therapy, and intervention of an autoimmune or inflammatory condition, disorder, or disease of a patient. In embodiments, the EMR 221 of the patient may be located within a dedicated facility, available from an external source (e.g., crowdsource, public database, etc.), and/or accessible via a communication network.

In embodiments, artificial intelligence engine 202 is configured to receive one or more inputs of data or datasets generated by artificial intelligence methods described further herein, wherein instructions for execution of such methods are stored on at least one cloud-based server 212. According to embodiments, the at least one cloud-based server 212 performs services/functions generally understood and referred to as "cloud computing," "on-demand computing," "software as a service (SaaS)," "platform computing," "network-accessible platform," "cloud services," "data centers," and the like. The term "cloud" generally encompasses a collection of hardware and software that forms a shared pool of configurable computing resources (e.g., networks, servers, storage, applications, services, etc.) suitably provisioned to provide on-demand self-service, network access, resource pooling, elasticity and measured service, among other features.

The artificial intelligence engine 202 may preferably be configured as a computational device wherein the hardware and/or software are configured to execute one or more instructions or algorithms from one or more module 214 to process one or more external data inputs. In various embodiments, the one or more module 214 comprise one or more measurement, risk and/or recommendation module. In embodiments, processed and predictive data or data sets of the one or more module 214, and clinical insights or recommendations generated by the artificial intelligence engine 202 are sent and stored on the one or more cloud based-based server 212 for distribution.

In embodiments, the at least one cloud-based server 212 comprises at least one software application (API) 216 configured to enable development of one or more software application product(s), or application(s) 218. Software applications 218 according to embodiments of the invention are configured to provide one or more functions, including but not limited to, data processing, data analysis, data presentation in graphical form, data annotation, recommendations, clinical insight, flare prediction, symptoms prediction, patient history, symptom trends, and the like. In various embodiments, the one or more application 218 comprises a system and methods for collecting, processing, and synthesizing clinical insights from at least one of: patient data, digital phenotype, patient medical record from an EMR database 221, outcomes data from an outcomes database 211, patient record relating to autoimmune, inflammatory condition, disorder, or disease, patient clinical notes, physician clinical notes, data from database residing on said cloud-based server 212, and results generated by at least one module 214, artificial intelligence engine 202.

In embodiments, at least one application 218 enables the retrieval or distribution of aggregated patient data generated by the module(s) 214 and/or from the artificial intelligence engine 202 to one or more payors for review. In certain embodiments, a provider user (e.g., healthcare provider) may access one or more application(s) 218 from a desktop client 220. Similarly, a patient user may not only generate data (e.g., patient-recorded outcomes, medication adherence, surveys, digital signature, digital phenotype, etc.), but can also send text messages, record videos, conduct video chats with clinicians, and/or access clinical insights and recommendations of healthcare providers from a mobile device (mobile client) 208. Alternatively, or in addition, a patient user can generate data, send text messages, communicate with clinicians, and access insights and recommendations from a mobile wearable device 224.

In embodiment, a mobile wearable device 224 may communicate with the artificial intelligence engine 202 via a cellular communication network 226, or indirectly with a mobile client 208 via Bluetooth, BLE, LAN, or the like. In certain embodiments, mobile device (mobile client) 208 comprises a mobile device application 222 configured to communicate with the at least one cloud-based server 212 via the communication network 226. In certain preferred embodiments, mobile device (mobile client) 208 comprises, as the at least one mobile device application 222 stored thereon, the providerAPP or the patientAPP described herein. Similarly, a desktop client 220 may be configured to access the at least one cloud-based server 212 via the communication network 226. In embodiments, communication network 226 is operably connected to and includes at least one of the following: LAN, WAN, wireless network, cellular network, and Internet connection.

As an object of the present disclosure, provided is an artificial intelligence system 200 and methods for the clinical management of autoimmune or inflammatory condition, disorders, and diseases. The artificial intelligence system/platform according to embodiments comprises an engine 202 that aggregates and analyzes healthcare data from a variety of sources and generates clinically validated diagnostic measures and recommendations to healthcare providers. The system 200 comprises one or more application(s), including a healthcare provider application (ProviderAPP) and a patient application (PatientAPP), communicably connected for the clinical management of patients. In embodiments, the engine 202 aggregates data from one or more application(s) 218, including from a ProviderAPP and a PatientAPP as described herein, and/or from a mobile wearable device 224, a Lab Information Management System (LIMS) 204, an environmental monitoring system 206, an EMR of the patient from an external database 222, a mobile client 208 and/or a desktop client 220. In embodiments, engine 202 analyzes the aggregate data using machine learning models, including (but not limited to) an artificial neural network or a deep learning neural network, to create diagnostic measures, predictions, and/or recommendations for one or more of a healthcare provider, clinician, digital health coach, and patient user.

An artificial intelligence system 200 according to embodiments of the invention comprises: interfaces for a patient, a healthcare provider, and a payer; at least one API 216; an engine 202; a mobile device 208 back end, and a data store residing on at least one cloud server 212. In embodiments, the system 200 comprises one or more external sources of data generation and/or storage medium, including, but not limited to, an EMR database 222, an external API 216, a Laboratory Information Management System (LIMS) 204, an environmental data source 206, and the like. According to embodiments, a healthcare provider can make clinical decisions based on analysis of the system 200 using a providerAPP 222. In embodiments, a patient is provided with a wearable digital technology device, such as a wearable device 224 and/or the mobile device 208, operable with the patientAPP 222.

In embodiments, a providerAPP 222 is configured to enable a provider to access the engine 202 and to prescribe one or more solution(s) to a patient. A provider can use providerAPP 222 to select at least one product selected from the group consisting of an intervention, prescription, recommendation, and prophylactic relating to an autoimmune or inflammatory condition, disorders, or diseases in prescribing the one or more solution(s) to the patient. ProviderAPP 222 may also be configured to allow a provider to view or receive results of a diagnostic measurement from LIMS 204, or a prediction or recommendations stored within an EMR database 210.

In embodiments, a patientAPP or mobile device application 222 is configured to enable a patient to collect or record medications, symptoms, adverse effect, adverse event, or other patient-reported outcomes. A portable computing device, such as a mobile wearable device 224 or mobile client 208, may preferably comprise a global position system (GPS) that automatically tracks location and environmental data of a patient user of the application 222. In certain embodiments, a mobile wearable device 224 or a mobile client 208 comprises at least one sensor of inertial measurement units (IMU), light, sound, humidity and/or touch, the at least one sensor being configured to capture and track a digital signal, signature, and/or derived digital phenotype relating to the patient user.

In further embodiments, a patient user of the at least one application 222, preferably including the PatientAPP, can access a mobile wearable device 224 using the at least one application 222 to collect data pertaining to the patient's activity, heartrate, sleep patterns, weight, body mass, blood pressure, exercise, etc. In still further embodiments, a patient user is able to message and/or conduct live video conferences with a healthcare provider or digital health coach or healthcare provider using the PatientAPP as the at least one application 222. The PatientAPP may be configured to enable raw message data or notes from the digital health coach or healthcare provider to be automatically captured by the PatientAPP and processed by the artificial intelligence engine 202. In still further embodiments, the PatientAPP 222 enables the recording of one or more digital phenotypes of a patient user. In summary, data from one or more digital technology device(s) (i.e., a mobile wearable device 224, mobile client 208, and desktop client 220) is processed and analyzed by the artificial intelligence engine 202, and one or more recommendations are sent to a patient using the artificial intelligence engine 202 of the system 200.

Figure 3:
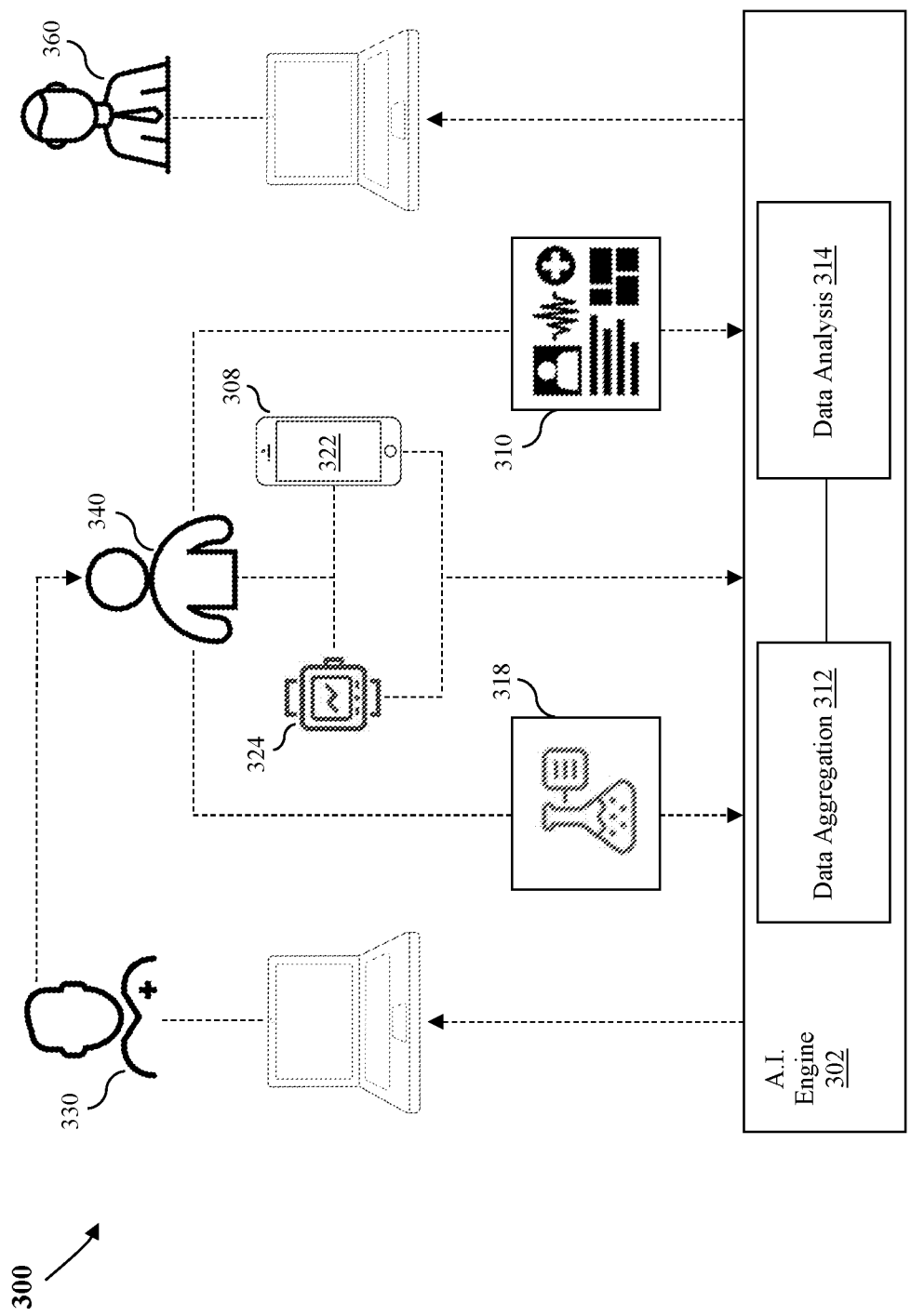
FIG. 3 is a functional diagram of a system according to embodiments of the invention.

Turning now to FIG. 3, provided is another functional diagram of a system 300 according to embodiments of the invention. Here, the system 300 comprises a healthcare provider portal 330, a patient portal 340, and a payer portal 360.

In embodiments, the patient portal 340 is configured to enable a patient user to download a PatientAPP 322, wherein the PatientAPP 322 is operably configured to measure data and data sets pertaining to patient training, validation, patient-reported outcomes and symptoms, diagnostic measures, analyte measurements, blood constituents, metabolites, drug concentrations, and the like. The data or data sets may be obtained from a data analyzer 318, a point of care self-testing device, a computing device 310 such as a desktop client, a mobile computing device such as a mobile client 308, wearable device 324, a portable EEG, a glucose meter, a wearable analytic device for measuring at least one autoimmune or inflammatory marker or biomarker, and the like. In embodiments, a patient portal 340 is configured to facilitate acquisition of a patient's blood sample, scheduling of a patient visit, and disseminating to the user one or more wearable device 324 or monitor. Thereafter, the patient's body fluid sample including blood undergoes laboratory analysis 318. To facilitate tracking of symptoms and treatments, also provided is one or more digital computing device 310 operable to collect data and communications from a healthcare provider, clinician, or health coach during one or more daily, weekly, monthly, or yearly sessions, for tracking of symptoms and treatment of the autoimmune or inflammatory condition, disorder, or disease.

In embodiments, the artificial intelligence engine 302 aggregates data 312 and stores the data in one or more database, data warehouse, and the like. In embodiments, the data is comprised of data from applications, including the PatientAPP and ProviderAPP 322, or from the one or more digital computing devices 310, an EMR database (221 in FIG. 2), LIMS (204 in FIG. 2) or an environmental data source (206 in FIG. 2). In certain embodiments, the artificial intelligence engine 302 generates results or insights for dissemination through the provider portal 330. In embodiments, the engine 302 employs an algorithm to analyze data 314 from the laboratory analysis 318 and/or the one or more digital computing device(s) 310 to generate reports, insights, and recommendations, for dissemination via a healthcare provider portal 330, patient portal 340, and/or payor portal 360.

In further embodiments, the system 300 is configured to enable continuous processing of analytical samples, digital data, aggregation of data, analysis of data, and dissemination of actionable data for the management of an autoimmune or inflammatory conditions, disorders, and diseases.

In certain embodiments, a payor portal 360 comprises one or more API further comprising a dashboard to enable a payor user access to the artificial intelligence engine 302 and to track one or more patient and/or provider metrics or a patient population. In embodiments, the artificial intelligence engine 302 aggregates data from one or more sources selected from a data warehouse, laboratory 318, mobile wearable device 324, an external EMR database, and one more application(s), the one or more application(s) comprising the PatientAPP and/or the ProviderAPP discussed herein.

In embodiments, one or more artificial intelligence algorithm is applied for data analysis 314 so as to generate a report and/or provide insights for a patient, provider, and/or payor. The one or more artificial intelligence algorithm is used to analyze data 314 in order to derive one or more digital phenotype or a diagnostic or predictive measure relating to an autoimmune or inflammatory symptom, condition, or disease of a patient.

An autoimmune disease, as used herein, includes (but is not limited to) Lupus erythematosus, cutaneous lupus erythematosus (CLE), disseminated lupus erythematosus (DLE) or systemic lupus erythematosus (SLE), chronic CLE, discoid lupus, tumid lupus, lupus pernio, lupus profundus (or panniculitis); subacute CLE (SCLE), acute CLE (ACLE), uveitis, Behcet's disease, sarcoidosis, Sjogren's syndrome, rheumatoid polyarthritis, juvenile polyarthritis, Fiessinger-Leroy-Reiter syndrome, gout, osteoarthritis, polymyositis, myocarditis, primary biliary cirrhosis, Crohn's disease, ulcerative colitis, multiple sclerosis and other demyelinating diseases, aplastic anemia, idiopathic thrombocytopenic purpura, any disease associated with non-tumor lymphoproliferation, B-cell lymphoma, Simmonds' panhypopituitarism, Basedow-Graves' disease and Graves' ophthalmopathy, subacute thyroiditis and Hashimoto's disease, Addison's disease, chronic hepatitis, and Type I Diabetes Mellitus.

Figure 4:
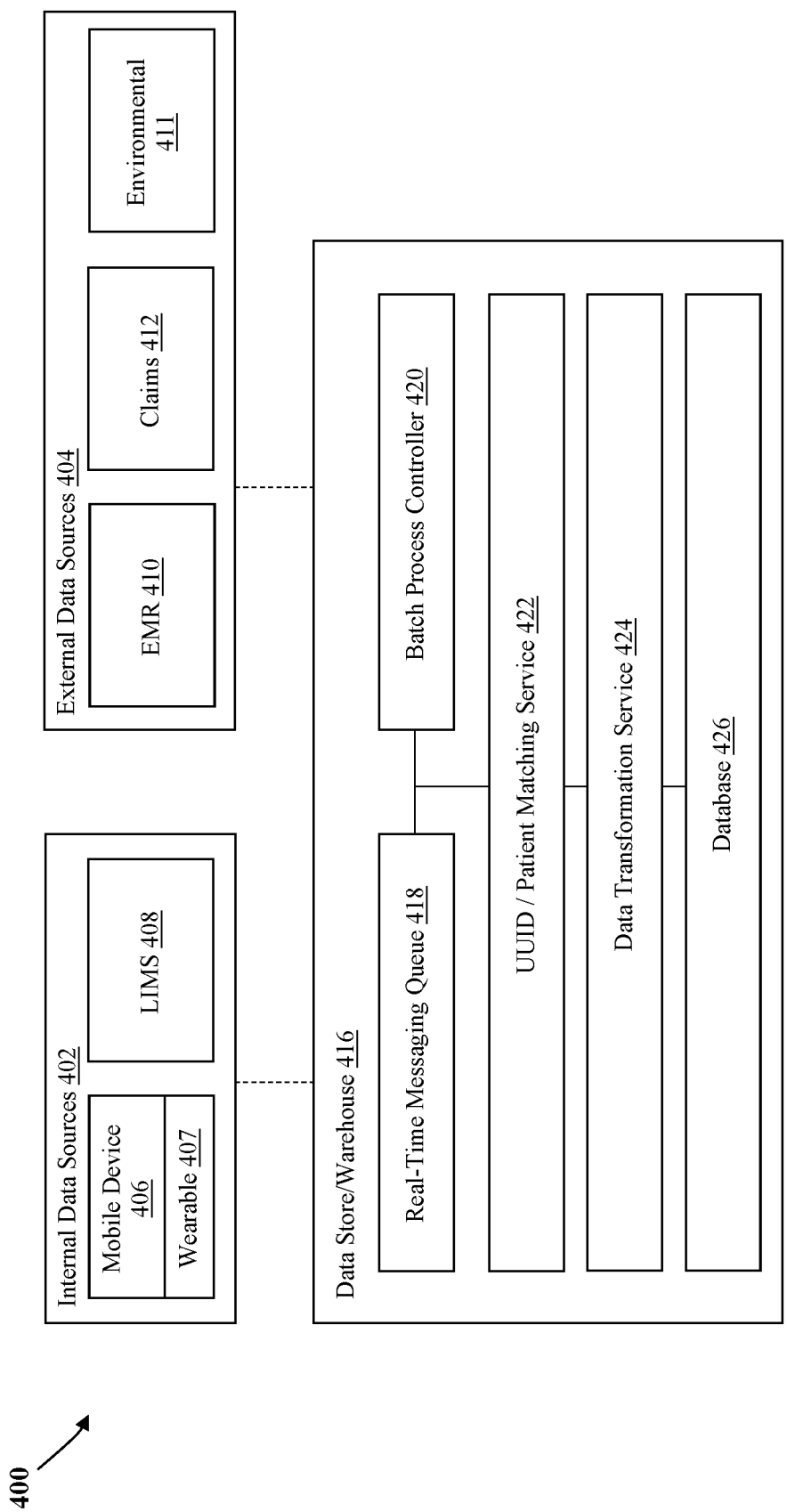
FIG. 4 is a block diagram illustrative of data configuration within the system of the invention.

Turning to FIG. 4, provided is a block diagram showing a representative data configuration framework 400 of a system according to embodiments of the invention. The data configuration framework (or architecture) 400 of the system preferably comprises one or more internal 402 and/or external 404 data sources. In embodiments, internal data sources 402 include one or more of a mobile device 406, a wearable device 407, device laboratory information management system (LIMS) 408, and the like. External data sources 404 include one or more of an EMR database 410, environmental monitoring system 411, and insurance claims 412. In embodiments, external data sources 404 may include data stored within at least one cloud-based server and data accessible via a communications network (see FIG. 2).

As depicted in FIG. 4, data from internal 402 and external 404 data sources are provided to a data store/warehouse 416. The data store/warehouse 416 comprises a real-time messaging queue 418 and a batch process controller 420, which further provide a Universally Unique Identifiers (UUID)/patient matching service 422, a data transformation service 424, and a database 426. In this way, data from various sources may be aggregated into a single or uniform dataset. In certain embodiments, data is transformed using external APIs. For example, weather APIs can be used to transform data provided in the form of GPS coordinates and a timestamp into environmental data (e.g., UV exposure and humidity) for a patient user.

In embodiments, data from the data store/warehouse 416 is processed according to a method comprising: (a) tagging the data with a UUID/Patient ID; (b) storing data in a data store/warehouse; (c) transforming the data; and (d) once tagged and transformed, storing the raw and clean data in a highly scalable database.

In step (a) of the above-exemplified method, data coming into the data store/warehouse 416 is associated to a patient user. In this regard, UUID/Patient Matching Service 422 accommodates differences from system to system for proper patient identification (herein after "ID") protocols. For example, a system receiving external laboratory results for a patient via facsimile will require that the data be associated with a patient using the PatientAPP. The Patient Matching Service 422 therefore creates a single ID for each unique patient and matches all data to that ID. Then, while raw data is stored in the data store/warehouse 416 in step (b), data is processed or transformed for model creation or production in step (c). Processing and/or transforming the data according to step (c) may comprise: augmentation (wherein additional data from external APIs is added, e.g., GPS coordinates and timestamps augmented with weather data); extraction (wherein certain data is not in a form that can be stored, e.g., data from PDFs); aggregation (wherein raw data needs to be combined or aggregated into new metrics, e.g., aggregating daily step count into weekly totals and or change metrics); conversion (where raw data entering the system includes different units of measurement); and cleaning (where data entering the system is not "clean" and thus needs to be further handled). Once data is tagged and transformed, in step (d) both the raw and cleaned data is stored in a highly scalable database 426.

In embodiment, data store/warehouse 416 comprises data feeds from various sources, including patient-reported data, clinical data, biological data, and pharmacy/payor data. Patient-reported data may include: medications taken, symptoms, and flare occurrences that have been logged by a patient user into a mobile application (e.g., the PatientAPP); surveys and tasks completed by the patient user in a mobile application (e.g., the PatientAPP); and messages from a digital health coach or medical service provider and notes of the digital health coach or medical service provider during video calls with the patient through applications such as the PatientAPP and ProviderAPP. Additional patient-reported data may also be provided by a wearable device 407 of the patient. Such data may include, e.g., step count data, heart rate data, sleep data, exercise data, and other vitals obtained by wearable devices (e.g., weight, blood pressure, and the like). In embodiments, an EMR database 410 serves as an external data source 404 from which clinical data of the patient may be obtained. Data from an EMR database 410 may include medication information of the patient, lab results, vitals and trends, vaccination history, health screening results, known allergies of the patient, medical procedures, referrals by physicians, and the like. In certain embodiments, the data warehouse 416 stores externally generated biological data, such as cytokine levels from CLIA Lab tests and biomarker scores of biological samples of the patient. In certain embodiments, externally generated data can include a patient's prescriptions with accompanying insurance claims 412 for the prescribed medications, as well as CPT codes and claims 412 provided by the patient's insurance payor.

Provided in Table 1 below are specific examples of data received from various data sources and processed within the data configuration framework of the system according to embodiments of the invention.

TABLE 1

| Type | Description | Process | Frequency | Fields |
|---|---|---|---|---|
| Patient Reported | Prescribed Medications | Real-time data from mobile app | As added by patient | user_id, name, RX ID, class, dosage, start date, end date, schedule |
| Patient Reported | Medications taken by patient | Real-time data from mobile app | As added by patient | user_id, name, med_id, log_time |
| Patient Reported | Symptoms | Real-time data from mobile app | As added by patient | user_id, symptom, severity, log_time |
| Patient Reported | Flare Report | Real-time data from mobile app | As added by patient | user_id, has_flare, flare_severity, flare_start, flare_stop |
| Patient Reported | Surveys | Real-time data from mobile app | As added by patient | user_id, survey_q_id, survey_responses, survey_user_response |
| Patient Reported | PRO Tasks | Real-time data from mobile app | As added by patient | user_id, pro_id, pro_q_id, pro_responses, pro_user_response |
| Patient Reported | Location Data | Real-time data from mobile app | As added by patient | user_id, geo_lat, geo_long |
| Patient Reported | Messages | Real-time data from mobile app | As added by patient | user_id, to_id, message_text, message_date_time |
| Patient Reported | Video Calls | Real-time data from mobile app | As added by patient | user_id, with_id, video_url, start_time, end_time |
| Patient Reported | Step Count | Real-time API data from wearable device | Every 6 hr or on sync based on wearable API | user_id. start_time, end_time, steps, distance, elevation |
| Patient Reported | Sleep | Real-time API data from wearable device | Every 6 hr or on sync based on wearable API | user_id, start_time, end_time, sleep_state, heart_rate, respiration_rate, snoring |
| Patient Reported | Heart Rate | Real-time API data from wearable device | Every 6 hr or on sync based on wearable API | user_id, start_time, end_time, device_id, wearposition, sampling_frequency, signal, heart_rate, hr_zone, heart_rate_varability |
| Patient Reported | Exercise Data | Real-time API data from wearable device | Every 6 hr or on sync based on wearable API | user_id, start_time, end_time, exercise_id, intensity, heart_rate, measure_device |
| Patient Reported | Vital Data | Real-time API data from wearable device | Every 6 hr or on sync based on wearable API | user_id, start_time, end_time, vital_id, vital_unit, vital_measure |
| Clinical | Medications | Batch data processed from EMR | Quarterly | user_id, name, RX ID, class, dosage, start date, end date, schedule, prescriber, pharmacy |
| Clinical | Lab Results | Batch data processed from EMR database | Quarterly | user_id, lab_test_id, lab_test_name, prescibe_date, prescriber_id, prescribing_facility_id, completion_date, completion_facility_id, lab_result, lab_report_url |
| Clinical | Vitals | Batch data processed from EMR database | Quarterly | user_id, start_time, end_time, vital_id, vital_unit, vital_measure, prescriber_id, prescribing_facility_id |
| Clinical | Vaccines | Batch data processed from EMR database | Quarterly | user_id, vaccine_id, vaccine_name, complete_date, facility_id |
| Clinical | Visits | Batch data processed from EMR database | Quarterly | user_id, facility_id, appt_schd_time, appt_completeion_time, visit_type_id |
| Clinical | Allergies | Batch data processed from EMR database | Quarterly | user_id, allergan_id, allegan_name, severity_id, symptoms |

TABLE 1-continued

| Type | Description | Process | Frequency | Fields |
|---|---|---|---|---|
| Biological (CLIA) | Protein Expressions | Real-time data from LIMS | As completed by the lab | user_id, start_time, end_time, lab_test_id, lab_facility_id, protein_id, protein_unit, protein_meaasurement |
| Biological (CLIA) | Scores | Real-time data from LIMS | As completed by the lab | user_id, start_time, end_time, lab_test_id, facility_id, score_unit, score, report_url |
| Payer/ Pharma | Prescriptions | Batch data processed from Claims | Quarterly | user_id, claim_id, claim_facility_id, start_time, end_time, prescription_id, pre_start_date, has_refill, billed_amount |
| Payer/ Pharma | Claims | Batch data processed from Claims | Quarterly; when filling script at pharmacy | user_id, claim_id, claim_facility_id, start_time, end_time, claim_event_id, event_start_date, billed_amount |

Figure 5:
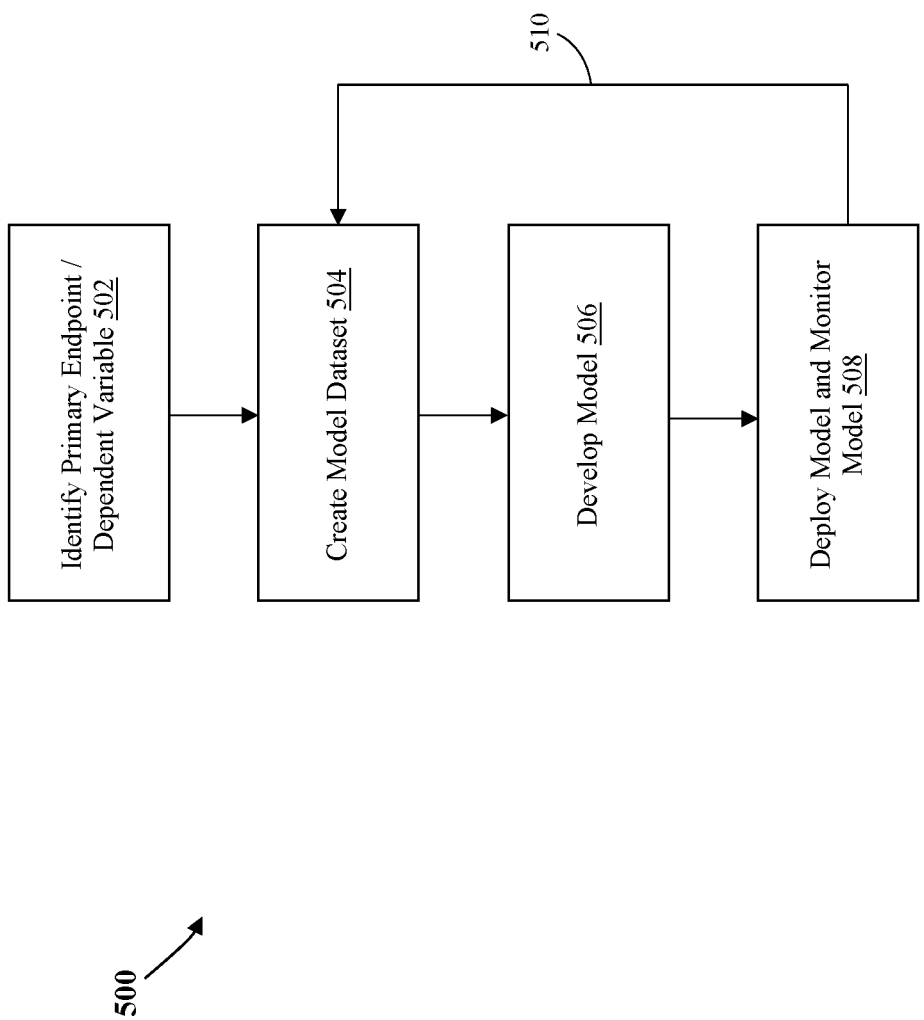
FIG. 5 a block diagram illustrating a process for development of a model system according to embodiments of the invention.

Turning now to FIG. 5, provided is a block diagram showing a general process of producing a model system for use in embodiments of the invention. Creation of a model system 500 according to embodiments of the invention begins with identifying a primary endpoint and/or dependent variable 502. The primary endpoint or dependent variable comprises at least one diagnostic, prognostic, or prodromal variable indicative of a patient's likelihood or probability of an onset or occurrence of a disease, condition, or symptoms (e.g., flares in a patient suffering from lupus). Examples of individual prodromal, diagnostic, and prognostic variables include (without limitation) physiological, biological, and external factors, such as, e.g., UV radiation from sun exposure, weather conditions (hot or cold temperatures and temperature changes), overheating, cooling, presence or risk of infection, lack of sleep/insomnia, work conditions, stress, strong chemical exposure, medication changes, fluorescent light exposure, food (e.g., spice, gluten, dairy, etc.), hormonal fluctuations, etc. Identification of one or more variable(s) as the primary endpoints in 502 will be determinative of one or more outputs.

Therefore, the step 502 of identifying an endpoint or dependent variable comprises determining or identifying a prodromal symptom, an actual symptom, a diagnostic measure, or a prognostic measure to enable generation of a linear or non-linear quantitative function, value, score, sale, measure, and the like. In embodiments of the invention, identification of a primary endpoint or dependent variable 502 enables generation of a linear or non-linear quantitative function, value, score, scale, measure, or the like.

Once an independent and/or dependent function has been determined for a variable with respect to a particular application, a model dataset can be created in step 504 by collecting or compiling data relating to the at least one independent prodromal symptom, actual symptom, diagnostic variable, or prognostic variable. Such data may include input data, such as patient-reported data, clinical data, and pharmacy data, physiological data, biological data, and data relating to external environmental factors that may affect immune function or causes an occurrence of symptoms in a patient (e.g., occurrence of flares). Examples of symptoms in a patient include (without limitation) rash, pruritus, pain, joint pain, joint swelling, stiffness, edema, abdominal pain, diarrhea, loss of appetite, muscle weakness, malaise, headache, migraine, body aches, fatigue, stress, infection, insomnia, temperature, anger, hormonal fluctuations, and the like. Examples of external factors include, e.g., stress, weather, temperature, temperature changes, humidity, natural UV radiation from the sun, artificially produced radiation such as fluorescent light, exposure to strong chemicals, work conditions, smoke, etc.

The additional steps of creating a model dataset 504, developing a model 506, and deploying and monitoring the model 508 in the creation of a model system are now further discussed in more detail with reference to FIGS. 6-8, respectively.

Figure 6:
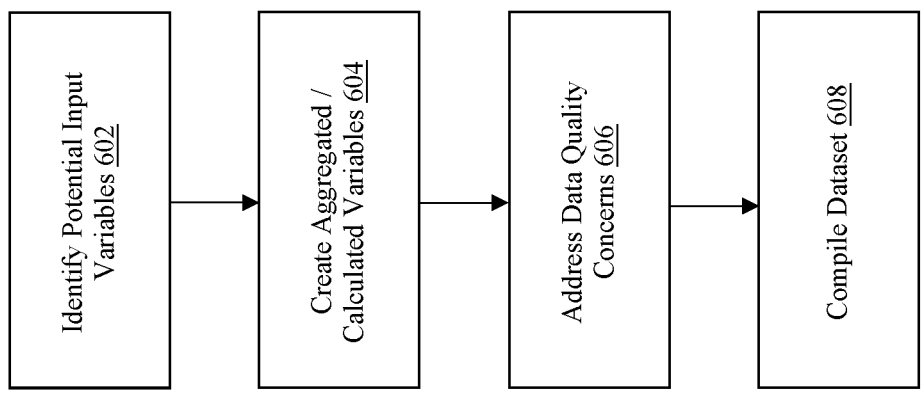
FIG. 6 is a block diagram illustrating a process for creation of a model dataset in the development of a model system according to embodiments of the invention.

Turning first to FIG. 6, provided is a block diagram of a process for creating a model data set 504. Specifically, creating a model data set 504 according to embodiments of the invention comprises: identifying potential input variables 602; creating aggregated/calculated variables 604; addressing data quality concerns 606; and compiling the dataset 608.

As discussed above, identifying potential input variables 602 comprises selecting input variables from at least one of a prodromal symptom, an actual symptom, a diagnostic variable, and a prognostic variable. Once an independent or dependent function has been determined for a particular application, one or more model dataset(s) can be created by incorporating input data, which may include any of patient reported data, clinical data, biological data, payer data, pharmacy data, EHR data, and the like.

Next, because the dataset for building a model comprises the analytical record, the raw input data is processed by creating aggregated/calculated variables 604. In the step of creating aggregated/calculated variables 604, raw input data can be rolled up to create new variables or to reduce the size of the input data. Types of data typically subject to aggregation include time series data, spatial data, and spatial-temporal data. For example, data of daily sleep hours can be rolled up to weekly or monthly sleep hours. In certain embodiments, one or more supervised or unsupervised, linear or non-linear, dimension reduction and/or data aggregation framework is applied. Suitable dimension reduction and data aggregation frameworks for use in embodiments of the invention include (without limitation): Principal Component Analysis (PCA), Multi-Dimension Scaling (MDS), Locally Linear Embedding (LLE), Independent Component Analysis, and Linear Discriminant Analysis. In certain embodiments, reducing dimensionality of input data comprises applying a PCA algorithm, resulting in output data that is orthogonal in the vector space. In certain embodiments, reducing dimensionality of input data comprises applying a Manifold Learning method to identify one or more non-linear structure(s) in the data. Manifold Learning methods are particularly useful for identifying high dimensional structures of raw input data from the data itself, without use of predetermined classifications.

In further embodiments, MDS is employed for projecting high dimensionality data into a lower dimensional surface. In such embodiments, observations include a similarity distance delta for input into the algorithm. Outcomes are provided as vectors of coordinates for each data point in a x-dimensional with the objective being to find representatives of K for a given input data set. The representatives of K are called "cluster centers" or "centroids," and are selected so as to have a minimum distance from each data point to a centroid in the same.

In still further embodiments, a lower dimension projection of a selected data set is identified or located using LEE, which preserves distances (location) within local neighborhoods. Furthermore, dimensionality of labeled data can be achieved using supervised methods, such as Linear Discriminant Analysis and/or Neighborhood Component Analysis.

The next step of addressing data quality concerns 606 is typically necessary due to the fact that raw data often includes incorrect information or is missing information. For this reason, this step typically comprises cleaning all input data before processing of such data by a machine learning model. All input data is first cleaned before being subject to processing by a machine learning model. Common data cleaning techniques suitable for use in embodiments of the invention include (without limitation) imputation, capping, and flooring of the data.

Data cleaning by imputation comprises the use of a decision tree, beginning by splitting the leaves off a tree until there's no more questions. In one embodiment, one or more leaf node comprising a class label with a majority of vote training examples reaching the leaf. In a preferred embodiment, each internal node represents a question on at least one feature that will be branching out according to the answers. Each answer generates a set of questions that aid to determine the data and decision-making based on it. The final result of decision tree indicates the possibility of all scenario of decision and outcome. In an alternative exemplary embodiment, K-nearest neighbor (KNN) is employed for imputation of missing data. KNN defines a set of nearest neighbors of a sample and substitutes the missing data by calculating the average of non-missing values to its neighbors. Nearest neighbor is measured as the closest values based on the Euclidean distance.

In certain embodiments, a "Bayesian network" may be employed for data input in the compiling of a dataset 608. Specifically, compiling a dataset 608 according to embodiments of the invention comprises employing one or more Bayesian network to apply additional independent constraints on variables so as to identify, in a concise manner, one or more probable relationship(s) between the variables. Using Bayesian networks for imputation offers several advantages, including the ability to handle missing data models encodes dependencies among all variables and the preservation of the joint probability distribution of the variables. A key element of the Bayesian approach is that missing data is incorporated as an added unknown quantity in estimating a posterior distribution, with the posterior distribution being defined as the total knowledge of integration between prior distribution and likelihood function to a parameter after it's been observed. In certain embodiments, particularly in models sensitive to high data input values, data cleaning may comprise calculating the mean (variance) by a method of capping and flooring of the input dataset or observations at one or more specific percentiles (e.g., 1% or 99%).

It is an object of the present disclosure to build computational predictive models capable of generalization of extracted or learned knowledge. Generalization is often interpreted as the broad ability of a machine learning model to handle new scenarios while overfitting is generally any undesirable degradation of performance. Poor generation is often characterized by over-fitting or over-training. A common method to avoid over-training is the use one or more Cross-Validation (CV) methods that requires appropriate data splitting. Accordingly, with reference being made to the general process of FIG. 500, the model dataset created in step 504 and depicted in FIG. 6 is used for developing at least one machine learning model. In embodiments, the model dataset created in step 504 constitutes the principal input in model development 506, as discussed in more detail below in reference to FIG. 7.

Figure 7:
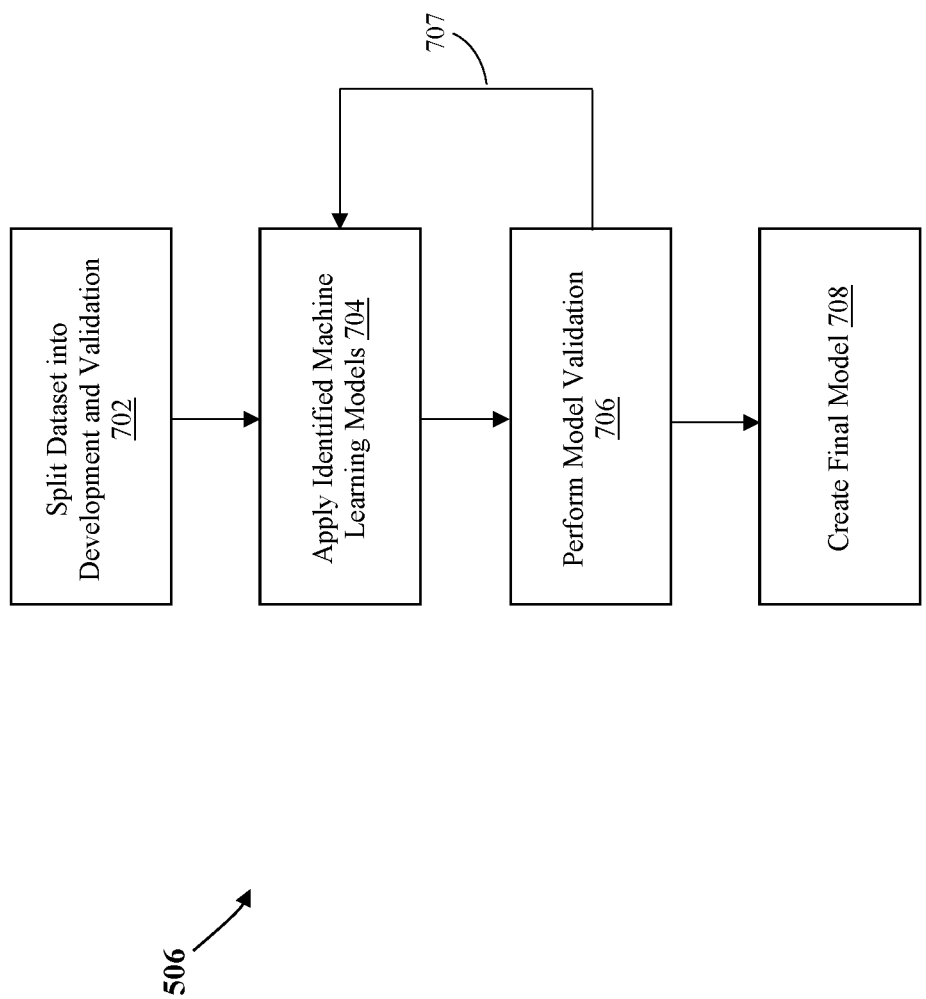
FIG. 7 is a block diagram illustrating a process for initial model development in the development of a model system according to embodiments of the invention.

With reference being made to FIG. 7, provided is a block diagram of a process for developing a model 506. As described in more detail below, the process comprises steps or processes for model variable identification, testing, validation and selection, and preferably incorporates the lowest possible number of variables. According to embodiments of the invention, model development 506 comprises: splitting the created dataset for development and validation 702; applying one or more identified machine learning model(s) 704; and performing model validation 706.

As discussed above, a method for avoiding over-training of a machine learning model is the use of one or more cross-validation (CV) method that requires appropriate data splitting. Therefore, in embodiments of the invention, the created dataset is subject to a splitting step 702, wherein the created dataset is split or divided into: (i) a training set (Ttr); (ii) a validation set (Tv); land (iii) a test set (Tte). Furthermore, data splitting 702 according to the disclosed methods may comprise simple random sampling (SRS) whereby samples are selected randomly with a uniform distribution. With SRS, each sample from a data subset (e.g., Ttr) will have an equal probability of selection. In certain embodiments, depending on the type of dataset compiled in 504, data splitting 702 comprises one or more statistical sampling method(s). Sampling methods suitable for use in embodiments of the invention can be divided into categories based on principles, goals and computational complexity, including (but not limited to) trial-and-error methods, systematic sampling, convenience sampling, CADEX, DUPLEX, and stratified sampling.

In certain trial-and-error sampling methods, a high variance of model performance may be evaluated using SRS by repeating a random sampling several times and averaging the results. Systematic sampling, on the other hand, is a deterministic approach for naturally ordered datasets, such as time series. Systematic sampling comprises identifying a proper ordering of a dataset, selecting a random starting sample, and then taking each kth sample from the ordered dataset. Convenience sampling is an efficient deterministic method widely used with time series wherein a dataset is split into discrete blocks, e.g. time intervals. The CADEX and its extension DUPLEX methods select samples based on their mutual Euclidean distance, starting with two most distances samples in a dataset and then repetitively selecting samples with maximal distance to the previously selected samples. Stratified sampling is typically used for measuring an internal structure and distribution of a dataset and then exploiting it to divide the dataset into relatively homogeneous groups of samples (strata, clusters) that are then separately selected from each cluster. Various clustering algorithms can be applied to divide a dataset into clusters, such as a c-means, fuzzy c-means, and self-organizing maps. including c-means, fuzzy c-means, and self-organizing maps. In a stratified random sampling method, samples from each cluster are selected with a uniform probability, with the number of samples chosen being selected per cluster or quota. Quota can be determined by one of the allocation rules such as equal allocation, proportional allocation, and optimal allocation.

Model development 506 according to embodiments of the invention further comprises a step 704 of applying one or more identified machine learning model(s) to the dataset. In embodiments, the one or more dataset(s) is applied into one or more identified, supervised or unsupervised, linear or nonlinear machine learning model trained to predict outputs of unknown dependent variables (e.g., dependent variable identified in 502 of FIG. 5) or a target function. A target function is represented by a finite training dataset of exemplary inputs (e.g., patient recorded, clinical, etc.) and the corresponding outputs.

To model time series phenomena, long short-term memory (LSTMs) and attention-based models can be employed to model time series phenomena. After an initial machine learning architecture with suitable training parameters is selected, the model can be trained using the Ttr dataset created in the splitting step 702. The model can then be evaluated iteratively using the additional Tv dataset and different models by varying training parameters to select the best performing model. The dataset Tte may be used to evaluate performance of a final model created according to embodiments of the invention.

Model development 506 according to embodiments of the invention comprises a third step 706 of performing model validation for robust generalization. Using cross-validation (CV) methods, accurate prediction and generalization constitute the balance between minimal bias and minimal variance of a model. A general goal of such cross-validation is an estimation of the performance of a learned model from available data using one or more algorithm(s) to gauge the model's generalizability. This can be achieved by comparing the performance of two or more different algorithms to identify the best algorithm for the available data, or, alternatively, comparing the performance of two or more variants of a parameterized model. For a chosen model, an estimate of a true error is required to assess performance. The true error rate of a model is the model's error rate when tested on an entire population data.

In general, CV methods applied according to embodiments of the invention require appropriate data splitting to have been performed (i.e., in step 702), as improper splitting of a dataset can lead to an excessively high variance in the model performance. In embodiments, a CV method comprises dividing the dataset into two subsets, with one subset being used for training and the other subset being used for evaluation of a final model. In certain embodiments, model validation 706 is performed using hold-out CV, wherein a dataset T (of size n) is separated into three mutually independent subsets: Training (Ttr), Validation (Tv), and Testing (Tte), the subsets having sizes "ntr," "nv" and "nte," respectively. The model is trained using the training subset Ttr, with performance of the model being periodically evaluated using the subset Tv to avoid over-training. Model training may be stopped when performance with the Tv subset is sufficiently close to a desired error rate or when improvement in performance stops.

To perform validation 706 according to embodiments of the invention, a dataset is divided into k different parts (referred to as "k-folds"). With a first part (or fold) held out as a validation set, the model is trained on the remaining (k−1) parts (folds). The model is then applied to the validation set and its predictive performance is recorded. This process is repeated k times with each part (fold) being held out as the validation set once. The recorded predictive performances are then averaged, and the optimal model parameter is established as the one with the best averaged predictive performance.

In embodiments where data is available, validation 706 can be performed using the above k-fold validation technique, or a 60-10-30 Ttr-Tv-Tte split. To illustrate by way of example: in a 5-fold CV, 80 percent of the original dataset is used for training (Ttr), 20 percent is used for validation (Tv), and, in the next iteration, another 20 percent of data is chosen as a test set (Tte), etc. This process is repeated five times until all data have served as Tv data once. Cross-validation is repeated with different parameter combinations, and once the best parameters have been found, the model is trained with the chosen parameters on all data that have previously been used for cross-validation and applied to the separate test sets.

In the event that there exists a serial correlation in the data, along with possible non-stationarities, a leave-one-out cross-validation (LOO-CV) technique is employed, wherein the k-fold is equal to the total number of available samples. An out-of-sample evaluation may also be performed, wherein a block of data from the end of a series dataset is used for evaluation. In certain embodiments, so-called "Monte Carlo" validation (i.e., bootstrapping) may be employed. Monte Carlo validation operates under similar principles as k-fold cross-validation, except that the folds are randomly chosen with replacement.

Model development 506 according to methods of the invention generally comprises one or more iterations 707 of model validation 706 to refine and ultimately create a final model 708. The models can be tuned, and final models selected based on performance/cost metrics and robustness. Automated tuning of models is based on varying the structure and hyperparameters to identify the best performing models. In embodiments, the final model can use any of the following metrics for optimization as appropriate: Cross Entropy for classification, and RMS Error for regression. To measure a model's overall performance, one or more metrics can be employed, such as, e.g., GINI (proxy of AuROC), KS Score, an event percent in top 3 deciles, with the top models being further evaluated and validated using an OOT dataset.

The final model created in step 708 is based on selection from different models with respect to, e.g., a regularized parameter, measured variable, or a particular set of features. Regularization refers to modification of a learning algorithm in favor of simpler prediction rules to avoid overfitting. In preferred embodiments, the final created model 708 predicts one or more outputs for the input samples from the training input dataset and is able to generalize to previously unseen data. If the model over-trains, it just memorizes the training examples and it is not able to give correct outputs also for patterns that were not in the training dataset. Good prediction via a training dataset and good generalization is known as the Bias and Variance trade-off.

Machine learning models suitable for use in embodiments of the present invention include: deep learning models, such as the deep Boltzmann machine, deep belief networks, Recurrent Neural Network (RNN), Fully Convolutional Neural Network (FCN), Dilated Residual Network (DRN), Generative Adversarial Network (GAN), and Deep Neural Network (DNN); ensemble, such as random forest, gradient boost machines, boosting, adaboosting, stacked generalization, and gradient boosted regression trees; neural networks, such as perception, back-propagation, Hopfield, ridge regression, LASSO, and elastic; rule systems, such as cubist, one rule, and zero rule; linear regression, such as ordinary least squares regression, stepwise regression, multivariate adaptive regression splines, locally estimated scatterplot smoothing, and logistic regression; Bayesian, such as naïve, averaged one-dependent estimators, Gaussian naïve, and multinomial naïve; decision tree, such as classification and regression, iterative dichotomiser, and condition-decision; instance-based, such k-nearest neighbor, learning vector quantization, and locally weighted learning; and clustering, such as k-means, k-medians, expectation max, and hierarchical.

Returning now to the general model development process 500 in FIG. 5, once a model has been developed 506, the model is deployed and monitored 508 in order to identify any refinements to be made to the initially created model dataset 504. Through an iterative feedback loop 510, based on results of monitoring of the deployed model 508, refinements can be made in the creation a model dataset 504.

In creating a model according to embodiments of the invention, one or more healthcare provider and/or patient are educated about, integrated into, and registered as users of system/platform. Once the at least one healthcare provider and/or patient are using the system, any new product or application can be additionally deployed within the system. Furthermore, any new diagnostic measure, prognosis, or recommendation identified in 502 can be added to one or more regular report(s) sent to a healthcare provider.

Following one or more reiterations of creating a model dataset 504, developing the model 506, deploying and monitoring the developed model 508 to identify refinements to be made in a subsequent creation of the model dataset 504, a resulting model preferably has an accuracy matching the accuracy calculated from validation of the model data set during model dataset creation 504. If at any time the model is found to have sub-optimal performance, the model can be rebuilt based on data obtained during monitoring of the deployed model 508.

Figure 8:
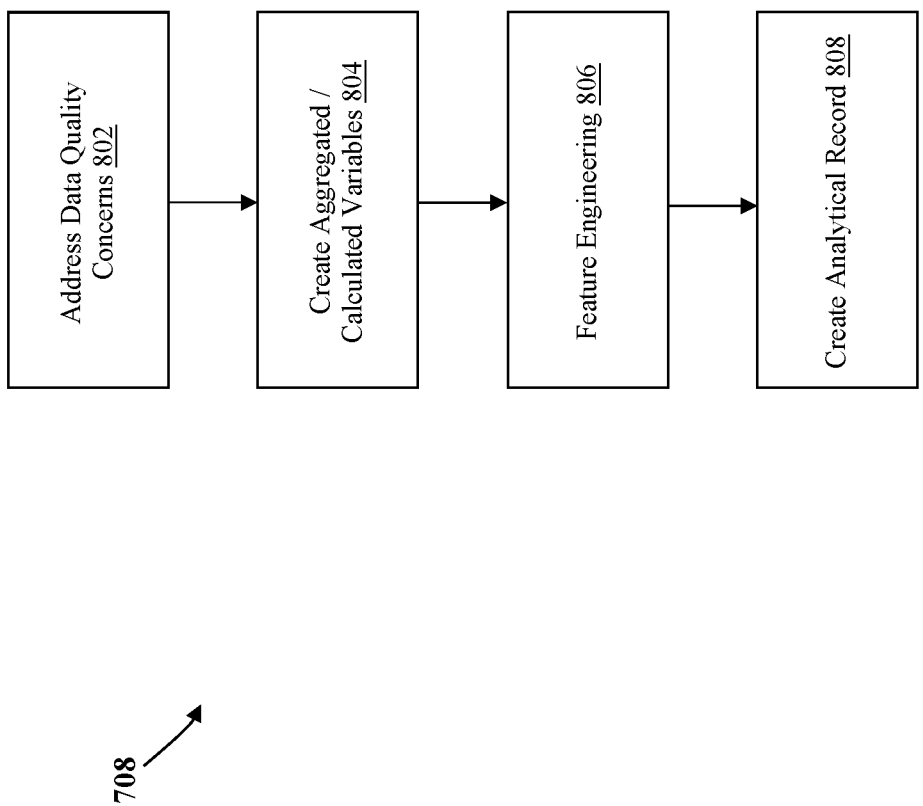
FIG. 8 is a block diagram illustrating a process for creating a final model in the development of a model system according to embodiments of the invention.

Turning to FIG. 8, provided is a block diagram showing in more detail the creation of a final model 708 according to embodiments of the invention. In creating a final model 708, raw input data is first transformed into clean analytical data. Examples of various categories of such raw input data are summarized in Table 2 below.

TABLE 2

| Data Type | Data Fields | Data Cleaning | Calculated Variables | Feature Engineering |
| --- | --- | --- | --- | --- |
| Raw Wearable Data | Raw Step Count, Raw Sleep, Raw Heart rate, Raw Vitals | Relatively structured, clean data | Daily, Weekly and monthly aggregates - daily averages. | Daily, weekly, monthly trends. |
| Summary Wearable Data | Activity summary, Sleep summary | Relatively structured, clean data | Daily, Weekly and monthly aggregates - daily averages. | Daily, weekly, monthly trends. |
| Patient Logged Activities | Exercise logged, Medication take logged, Symptom logged, Flare Logged, Survey completed, PRO completed, Medication Added, Medication Changed | Standardized Medication, Calibrate Flares. | Trends, Ratios (e.g. # of certain symptoms per flare), Indicators (exercise resumed # days after flare) | TME/One-hot/Frequency/WoE encoding |
| Patient Logged Symptoms | Symptom details, Flare details | User entered, structured input will be provided with some freeform. Freeform needs cleansing. | Severity, frequency, duration, category of symptoms and flares. | Binary/Graded scale to label symptoms - used as target variable, and potentially as attributes for future flares and acute incidents |
| Environmental Data | Geo coordinates, weather, allergy, UV, socioeconomic, social determinants | Diverse data requiring multiple cleansing, transformation, MVI methods | Higher level classifications/ buckets (high/low/medium or scaled), may use further structuring by type of allergy etc. | target mean encoded zipcodes, socio-economic slabs, social determinants |
| Patient Conversation Data | Messages with health coach, notes from health coach | Standardize and infer from text | Messages, notes converted to pre-determined numerical scores for attributes. | TME/One-hot/Frequency/WoE encoding |

TABLE 2-continued

| Data Type | Data Fields | Data Cleaning | Calculated Variables | Feature Engineering |
|---|---|---|---|---|
| Patient Structured Responses | Survey response, PRO response | Standardize and infer from any free form input | Survey response mapped to pre-determined numerical scores | TME/One-hot/Frequency/WoE encoding |
| Demographic Data | Age, gender, conditions, income, education, ethnicity, family history, current medications, previous medication, treatment history, allergies, vaccines | MVI based on similarity indices - within clusters | Standardize and bucketize attributes (age, income, education buckets) | TME/One-hot/Frequency/WoE encoding |
| Clinical Results Data | Lab results, vitals, Progentec lab results, Progentec scores | Infer from any freeform text or canned descriptions. | Standardized scores, longitudinal data. Trends of specific vitals, lab metric and results. | TME/One-hot/Frequency/WoE encoding |
| Clinical Treatment Data | Visits, hospitalizations, decisions | Standardization of visit, hospitalization, decision types. | Severity, Frequency, Duration - scored on a predetermined scale. Trends, #occurences in the past <n> months, residual impact of decisions (subjective scoring) | Visits and Hospitalizations as labels/target variables, as well as longitudinal attributes. Decisions incorporated as longitudinal attributes |
| Claims Data | Claims | Infer visits, hospitalizations from claims data where possible. | Scored on a predetermined scale. Trends of claims, categorized by type and tagged to visits and hospitalization instances. | Trend metrics, ratio variables w.r.t visits |

In creating a final model 708 according to methods of the invention, raw data input is processed in order to: address any data quality concerns in step 802; create aggregated or calculated variables in step 804; and engineer features of the data in step 806. In the first step 802, raw data input is examined to address potential data quality issues or concerns, such as, e.g., outliers or missing values. For example, as shown in Table 2 above, raw data from a wearable device may be in the form of step count signals, one or more of which may be filtered to remove noise. In the step of creating aggregated/calculated variables 804, the raw input data may be reduced in size or rolled up to create new variables.

Types of data typically subject to aggregation include, e.g., time series data, spatial data, and spatial-temporal data. In embodiments, one or more supervised or unsupervised, linear or non-linear, dimension reduction and/or data aggregation framework is applied. Suitable frameworks for application include those discussed herein with reference to step 604 depicted in FIG. 6. Taking as an example the data category of Patient Reported Symptoms in FIG. 2 above, the calculated variable representing the pain symptoms experienced by the patient is the resulting value after applying a Visual Analog Scale (VAS). Then, in the step 806, the cleaned and aggregated dataset is subject to feature engineering. The step of feature engineering 806 relies on domain knowledge of the dataset in order to create features for implementation into one or more machine learning methods of the invention.

In various embodiments, given a model, machine learning comprises learning one or more parameters of a model based on patterns and inferences. The number of parameters depends on the number of predetermined or predictive features available. In various embodiments, one or more parameter is estimated by optimizing one or more objective or cost function. For example, one objective function is the Conditional Log-Likelihood, and another is the Log-Likelihood. In an exemplary embodiment, feature engineering comprises regulation, use of domain knowledge, exploitation of existing structure in the data, dimensionality reduction, or the use of data to build features. As an example, in reference to the Table Category of "Raw Wearable Data," feature engineering enables the identification of a patient's activity as walking or jogging. In a similar manner, in reference to the Table Category "Patient Logged Symptoms," feature engineering enables the identification of a patient's symptom as No Pain through image recognition of a smiley face drawn within a patient's log. More complex features can also be created using statistics and machine learning methods. An object of the present disclosure comprises the automated feature generation and selection. A number of automated features can be generated using methods, including but not limited to, the combination of tuples and triples, and use a number of additional encoding techniques such as PCA, Clustering—(KNN, K-Means), WoE, Target Mean, Helmert, Binary, Frequency encoding on the generated variables. For automated feature selection, the features can be culled based on various metrics taking into consideration Variable Importance and Multi-Collinearity. This culled set of metrics can be further refined based on explain-ability. Finally, an analytical record is created in step 808, the analytical record constituting the primary input for creating a final machine learning model according to the present invention.

As discussed herein, an object of the present invention is to provide a platform or system for management of patients having, or at risk of having, an autoimmune or inflammatory condition, disorder, or disease. In specific embodiments, suitable patient candidates include, and can be generally divided into the following categories: (a) persons not yet diagnosed with Lupus; (b) persons recently/newly diagnosed as having Lupus; and (c) persons actively managing Lupus. Various different parameters, demographics, diagnostic measures, and scoring criteria can be used to for classification of patients into and within each of the above categories. Provided in Tables 3-5 below are examples of classifications and associated recommendations for patients of each of the above categories (a)-(c) as employed in various embodiments of the present invention.

In embodiments, a patient can be a person with Lupus, falling under category (a) above. Identification or classification of a person in this category may include the exemplified diagnostic evaluations and subsequent recommendations summarized in Table 3 below.

TABLE 3

PATIENTS NOT YET DIAGNOSED WITH LUPUS

| Classification Source | Classification Objective | Correlation of Data | Example |
|---|---|---|---|
| Evaluations | Risk of Lupus | Diagnostic measure provides a % score representing a patient's risk for developing Lupus. | Based on the patient's medical history, symptoms, and biomarkers, there is a [80%] chance of the patient developing Lupus. |
|  | Likelihood of Lupus | Diagnostic measure provides a score representing a likelihood that the patient in fact has Lupus. | Based on the patient's calculated risk (above), and analyzing symptoms, there is a 95% likelihood that the patient has Lupus. |
| Recommendations | Accurate Diagnosis Reducing Discomfort | Confirm accuracy of initial Lupus diagnosis. Alleviate current symptoms prior to actual diagnosis of Lupus. | Patient should log sleep patterns and temperature. Patient should do daily exercises alongside medication. |

In alternative embodiments, a patient can be a person recently diagnosed with Lupus, falling under category (b) above. Classifications of persons within this category may be based on and include the exemplified diagnostic evaluations and subsequent recommendations summarized in Table 4 below.

TABLE 4

PATIENTS RECENTLY DIAGNOSED WITH LUPUS

| Classification Source | Classification Objective | Correlation of Data | Examples |
|---|---|---|---|
| Evaluations | Lupus Stage | Diagnostic measures provide a score representative of current stage or state of progression of Lupus in the patient. | Diagnosed patient has early stages of Lupus disease progression. |
|  | Lupus Severity | Diagnostic measures provide a score representative of the likelihood that the patient will develop (i) low, (ii) mild, (iii) moderate, or (iv) severe Lupus disease activity. | Diagnosed patient has a [77%] chance of experiencing severe Lupus symptoms, which is [2.3%] higher than the average patient diagnosed with Lupus. |
|  | Prediction of Medication Efficacy | Diagnostic measures provide a score representative of the likelihood that a particular Lupus medication will be effective for treating a recently diagnosed patient. | There is a [87%] chance of a positive treatment response to [MTX], which is [4.5%] greater than an average patient diagnosed with Lupus. |
|  | Prediction of Patient Risk | Diagnostic measures provide a score representative of the likelihood that a recently diagnosed patient will develop health complications due to both personal challenges (e.g., adherence) and clinical risks (e.g., other medical conditions or diseases). | There is a [78%] chance of developing [cardiovascular disease], which is [8.2 times more] than the average patient diagnosed with Lupus. |

TABLE 4-continued

PATIENTS RECENTLY DIAGNOSED WITH LUPUS

| Classification Source | Classification Objective | Correlation of Data | Examples |
| --- | --- | --- | --- |
| Recommendations | Initial Treatment | Clinical recommendation for immediate treatment of a patient recently diagnosed with Lupus. | Disease management will be best achieved by starting the patient on [HCQ and 3.5 mg Prednisone]. |
| | Treatment Plan | Clinical recommendation of a treatment plan for a patient recently diagnosed with Lupus. | Long-term disease management will be best achieved by starting the patient on a diet plan and a mental wellness plan. |
| | Physician Matching | Recommendation of a physician well suited to provide care for a patient recently diagnosed with Lupus. | [Doctor] is the best match based on the patient's preferences and the provider's experience. |
| | Education Plan | Recommendation of an education plan most appropriate for a patient recently diagnosed with Lupus. | Long-term disease management will be best achieved by educating the patient. |

In embodiments, a patient can be a person who is already managing Lupus under category (c) above. Classifications of persons within this category may be based on and include the exemplified diagnostic evaluations and subsequent recommendations summarized in Table 5 below.

TABLE 5

PATIENTS DIAGNOSED WITH AND MANAGING LUPUS

| Classification Basis | Classification Objective | Correlation of Data | Examples |
| --- | --- | --- | --- |
| Evaluations | Lupus Activity | Diagnostic measures provide a score representative of the current disease activity of a Lupus patient. | The current disease activity of the patient is [55 out of 100]. |
| | Prediction of Medication Efficacy | Diagnostic measures provide a score representative of the likelihood a particular medication will be effective for a Lupus patient. | There is a [87%] chance that the patient will have a positive treatment response to [MTX], which is 4.5 times greater than the average Lupus patient. |
| | Flare Prediction Index | Diagnostic measures provide a score representative of the likelihood that the patient will have a Lupus flare in the next 8-12 weeks. | The patient has a [92%] chance of experiencing a Lupus flare in the next 8-12 weeks. |
| | Change in Efficacy of Treatment | Diagnostic measures provide a score representative of the likelihood that a patient's current treatment plan is no longer effective and needs to be modified. | There is an 88% chance that the current treatment plan is no longer effective and needs to be changed. |
| | Disease Maturity | Diagnostic measures provide a score representative of the current stage of progression of Lupus. | The patient is still in early stages of Lupus disease progression. |
| | Patient Segmentation | Diagnostic measures provide a classification representative of a cluster or group of Lupus patients with similar characteristics, which can be used in conjunction with other measures. This would be used in conjunction with other measures and recommendations. Example: Lupus patient is classified as a 23-A patient. | The patient is classified as a [23-A] patient. |
| | Organ Damage Index | Diagnostic measures provide a score representative of the level of damage to a Lupus patient's organs. | The patient's organ damage index is [88 out of 100]. |

TABLE 5-continued

PATIENTS DIAGNOSED WITH AND MANAGING LUPUS

| Classification Basis | Classification Objective | Correlation of Data | Examples |
|---|---|---|---|
| | Treatment Adherence | Diagnostic measures provide a score representative of the level of adherence a patient has to their current treatment plan. | The patient's treatment adherence is [77 out of 100]. |
| | Co-Morbidity Impact | diagnostic measure that provides a score that represents the level of impact a particular co-morbidity has on lupus disease activity. | The patient's depression has a HIGH impact on Lupus disease activity. |
| | Prediction of Patient Risk | Diagnostic measures provide a score representative of the likelihood a Lupus patient will develop a particular risk. | The patient has a [78%] chance of developing [heart disease], which is [8.2 times more] than the average Lupus patient. |
| Recommendations | Treatment Plan | Recommendation of the next best treatment plan for a Lupus patient. | Continued long-term disease management will be best achieved by shifting the patient to [diet plan A] from [diet plan C] and starting a mental wellness plan. |
| | Adherence Plan | Recommendation of the best adherence plan for a lupus patient. Example. Treatment adherence can be improved by starting this patient on adherence plan B.) | Treatment adherence can be improved by starting [adherence plan]. |

Figure 9:
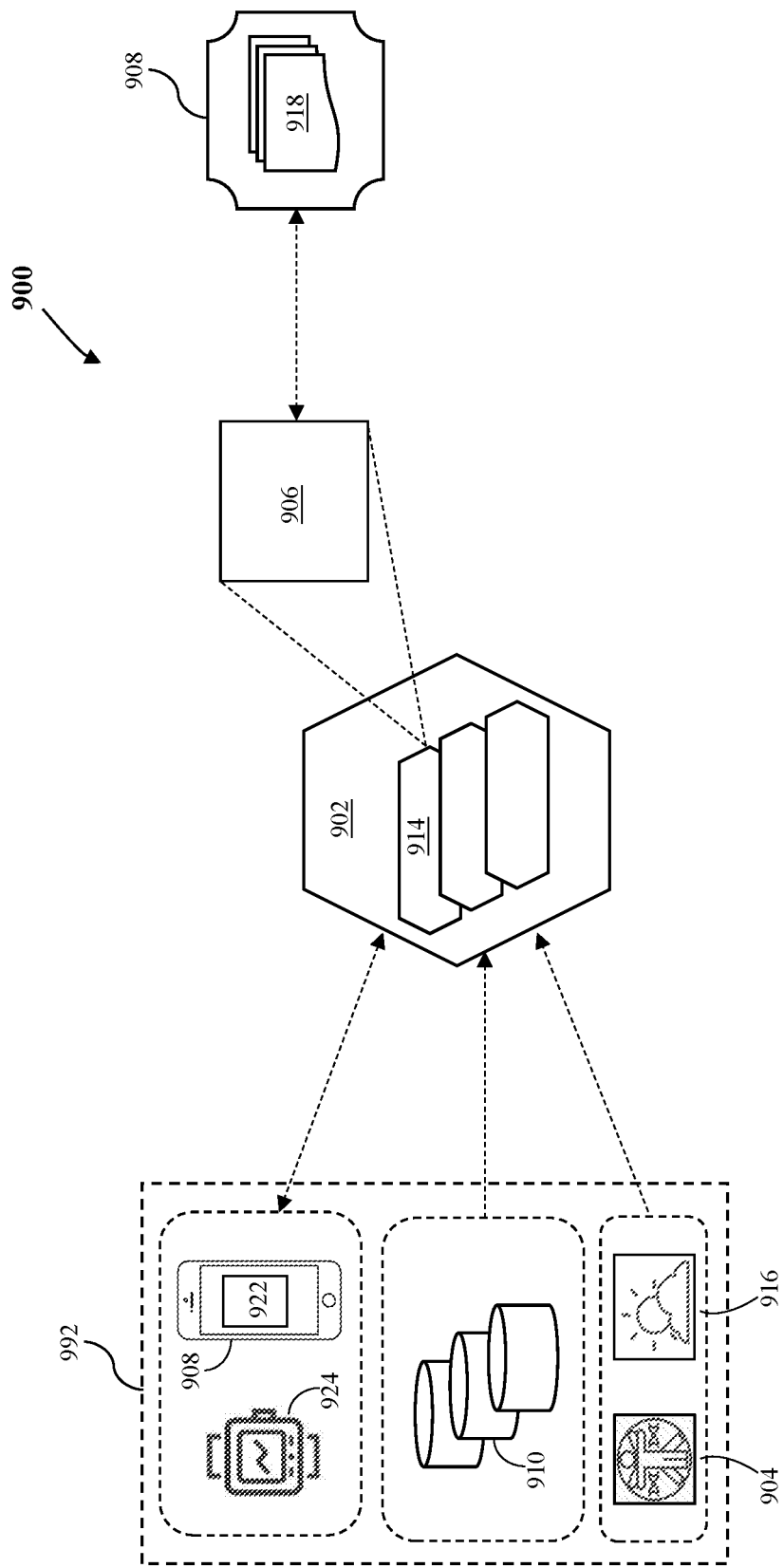
FIG. 9 is a functional diagram of a system, and a diagnostic module thereof, according to embodiments of the invention.

Reference is now made to FIG. 9, showing a functional diagram of a system 900 according to embodiments of the invention, with focus on a diagnostic module 914 thereof. In the system 900, one or more module 914 within an artificial intelligence engine 902 collects data generated by at least one patient data source 992. In embodiments, the data source 992 comprises data generated by a mobile client 908 and/or a mobile application 922. In preferred embodiments, the data source 992 comprises data generated by a mobile application 922. In preferred embodiments, the mobile application 922 comprises a patientAPP as described herein. In certain embodiments, the data source 992 comprises data generated by an EMR database 910, LIMS 904, and/or environmental tracking system 916. Input data may be selected from one or more of the following: Raw Wearable Data; Summary Wearable Data; Patient Logged Activities; Patient Logged Symptoms; Environmental Data; Patient Conversation Data; Patient Structured Responses; Demographic Data; Clinical Results Data; Clinical Treatment Data; and Claims Data.

In embodiments, the at least one module 914 of an artificial intelligence engine 902 is configured to process data from one or more data source 992 to provide at least one diagnostic measure via a score 906, the at least one diagnostic measure being representative of a current state of an autoimmune or inflammatory condition, disorder, or disease state of a patient. The at least one score 906 is disseminated to a patient, provider, or payer portal via one or more external API 908 (e.g., through a desktop client 220 or mobile client 208 shown in FIG. 2), and/or through one or more application 918 thereof. In embodiments, the at least one score 906 enables a patient, provider, or payer to be provided with access to at least one model, insight, or claim, including (but not limited to): Lupus Classification, Disease Age, Physician Match, Lupus Disease Activity, Treatment Efficacy Change, Patient Segmentation, Organ Damage Index, Treatment Adherence, Co-Morbidity Impact, or the like. A claim may include the following types of data: Co-Morbidity Impact, Disease Age, Lupus Classification, Lupus Disease Activity, Organ Damage Index, Patient Segmentation, Physician Match, Treatment Adherence, and Treatment Efficacy Change.

Figure 10:
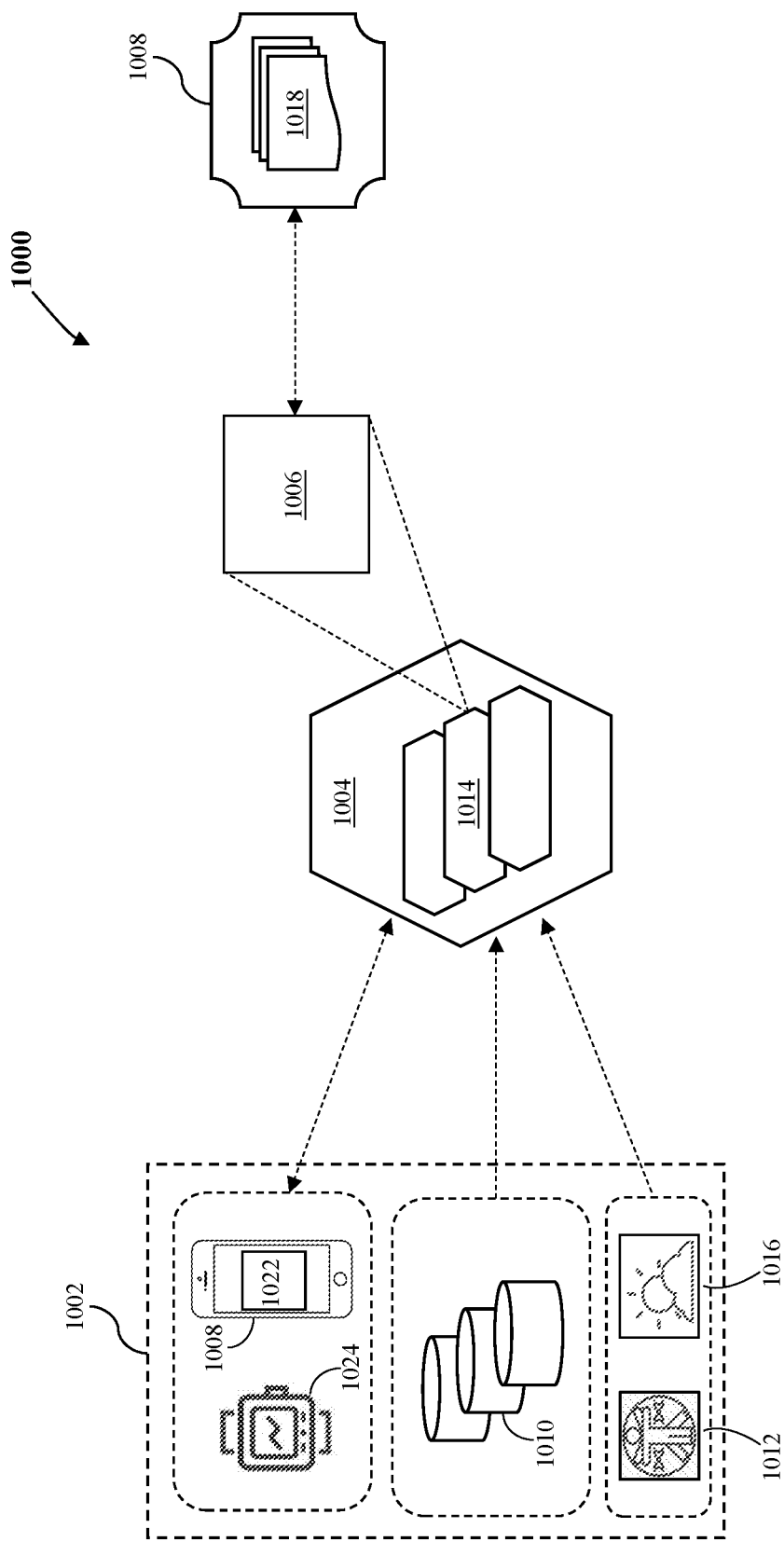
FIG. 10 is a functional diagram of a system, and a risk module thereof, according to embodiments of the invention.

Turning to FIG. 10, provided is a functional block diagram of a system 1000 according to additional embodiments of the invention, with focus on a risk module 1014 thereof. In the system 1000, one or more module 1014 within an artificial intelligence engine 1004 collects data generated by one or more patient data source 1002. In an exemplary implementation, the data source comprises data generated by a mobile client 1008 and/or a mobile application 1022. In preferred embodiments, the mobile application 1022 comprises a patientAPP as described herein. In another exemplary implementation, the data source 1002 comprises data generated by EMR 1010, LIMS 1012, and/or environmental tracking system 1016. Input data may be selected from one or more of the following: Raw Wearable Data; Summary Wearable Data; Patient Logged Activities; Patient Logged Symptoms; Environmental Data; Patient Conversation Data; Patient Structured Responses; Demographic Data; Clinical Results Data; Clinical Treatment Data; and Claims Data.

In embodiments, the at least one module 1014 of an artificial intelligence engine 1004 is configured to process data from one or more data source 1002 to provide at least one risk measure via one or more score 1006, the at least one risk measure being representative of the likelihood of a future state of an autoimmune or inflammatory condition, disorder, or disease in a patient. In embodiments, estimating performance of a learned model from available data comprises using one or more algorithm to gauge the generalizability, comparing performance of two or more different algorithms, and selecting the most optimal algorithm from selected data, or alternatively comparing the performance of two or more variants of a parameterized model. For a selected model, an estimate of a true error is required to assess performance. The true error rate is a model's error rate when tested against an entire population data.

In embodiments, at least one score 1006 is disseminated to a patient, provider, or payer portal via one or more external API 1008 (e.g., through a desk top client 220 or mobile client 208 as shown of FIG. 2), and/or through one or more application 1018 thereof. The at least one score 1006 enables a patient, provider, or payer to be provided with access to least one model, insight, or claim(s), including but not limited to, Lupus Development Risk, Severity Prediction, Medication Efficacy Prediction, Patient Risk Prediction, Flare Prediction Index, or the like. An identified risk enables one or more claim, including, e.g., Flare Prediction Index; Lupus Development Risk; Medication Efficacy Prediction; Patient Risk Prediction; and Severity Prediction.

Figure 11:
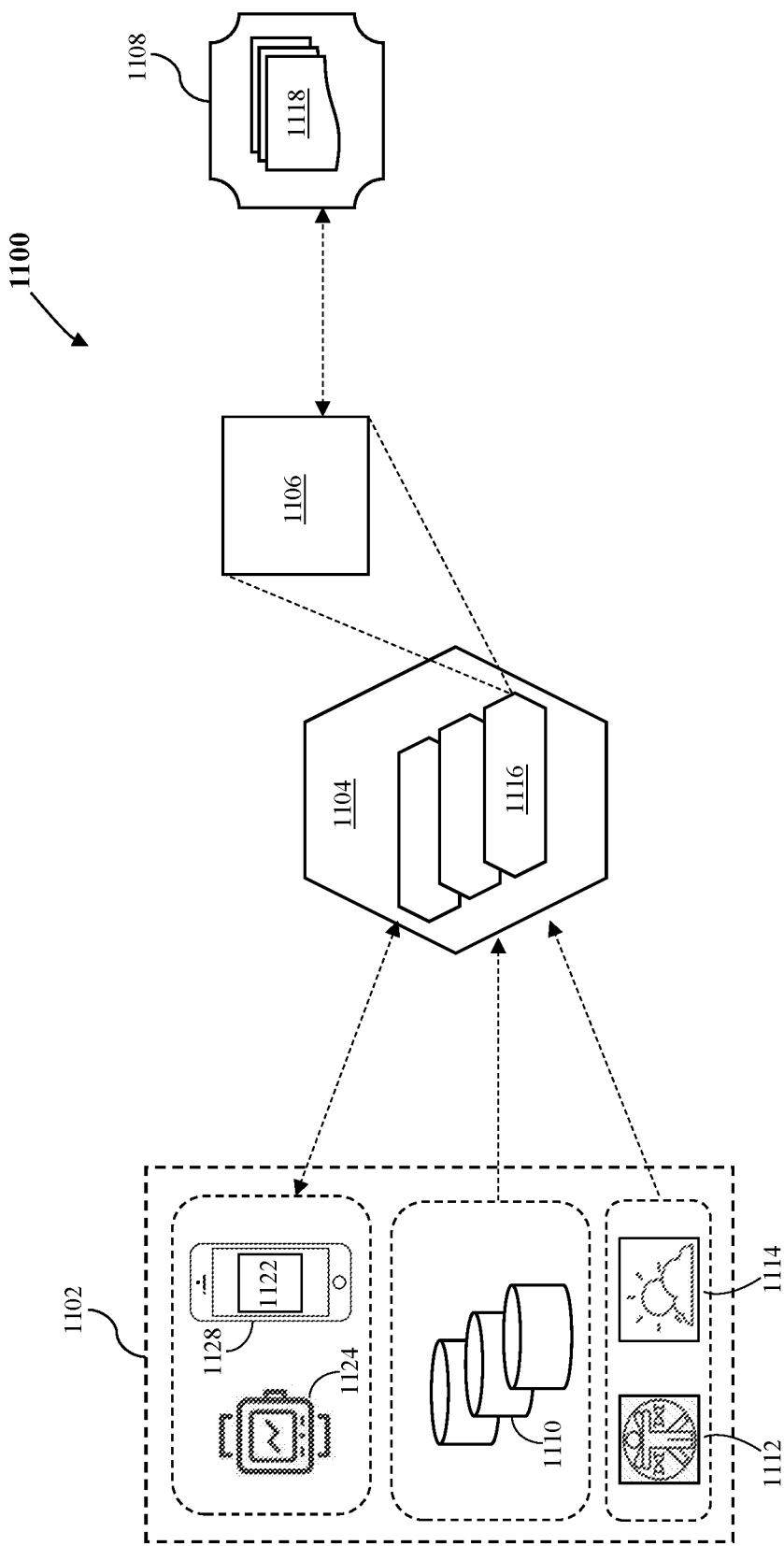
FIG. 11 is a functional diagram of a system, and a recommendation module thereof, according to embodiments of the invention.

Referring now to FIG. 11, provided is a functional block diagram of a system 1100 according to still further embodiments of the invention, with focus on a recommendation module 1116 thereof. In the system 1100, one or more module 1116 within an artificial intelligence engine 1104 collects data generated by one or more patient data source 1102. In an exemplary implementation, the data source comprises data generated by a mobile client 1128 and/or a mobile application 1122. In preferred embodiments, the mobile application 1122 comprises a patientAPP as described herein. In another exemplary implementation, the data source 1102 comprises data generated by EMR 1110, LIMS 1112, and/or environmental tracking system 1114. Input data may be selected from one or more of the following: Raw Wearable Data; Summary Wearable Data; Patient Logged Activities; Patient Logged Symptoms; Environmental Data; Patient Conversation Data; Patient Structured Responses; Demographic Data; Clinical Results Data; Clinical Treatment Data; Claims Data.

In embodiments, the at least one module 1116 of an artificial intelligence engine 1104 is configured to process data from one or more data source 1102 to provide at least one recommendation 1106, the at least one recommendation being an activity, therapy, or treatment that will improve outcomes of a patient having autoimmune or inflammatory condition, disorder, or disease. In embodiments, the at least one recommendation 1106 is disseminated to a patient portal via one or more external API 1108 (e.g., through a desk top client 220 or a mobile client 208 as shown in FIG. 2), and/or through one or more application 1118 thereof. In embodiments, the one or more recommendation 1106 enables a patient, provider, or payer to be provided with access to at least one model, insight, or claim(s), including but not limited to, a Lupus Diagnostic Journey NBA, Symptom Relief NBA, First Therapy Recommendation, Treatment Plan Recommendation, Education Plan Recommendation, Adherence Plan Recommendation, Patient Risk Prediction, or the like. In various embodiments, a recommendation comprises one or more of a Lupus Diagnostic Journey NBA, Symptom Relief NBA, First Therapy Recommendation, Treatment Plan Recommendation, Education Plan Recommendation, Adherence Plan Recommendation, and Patient Risk Prediction.

Figure 12:
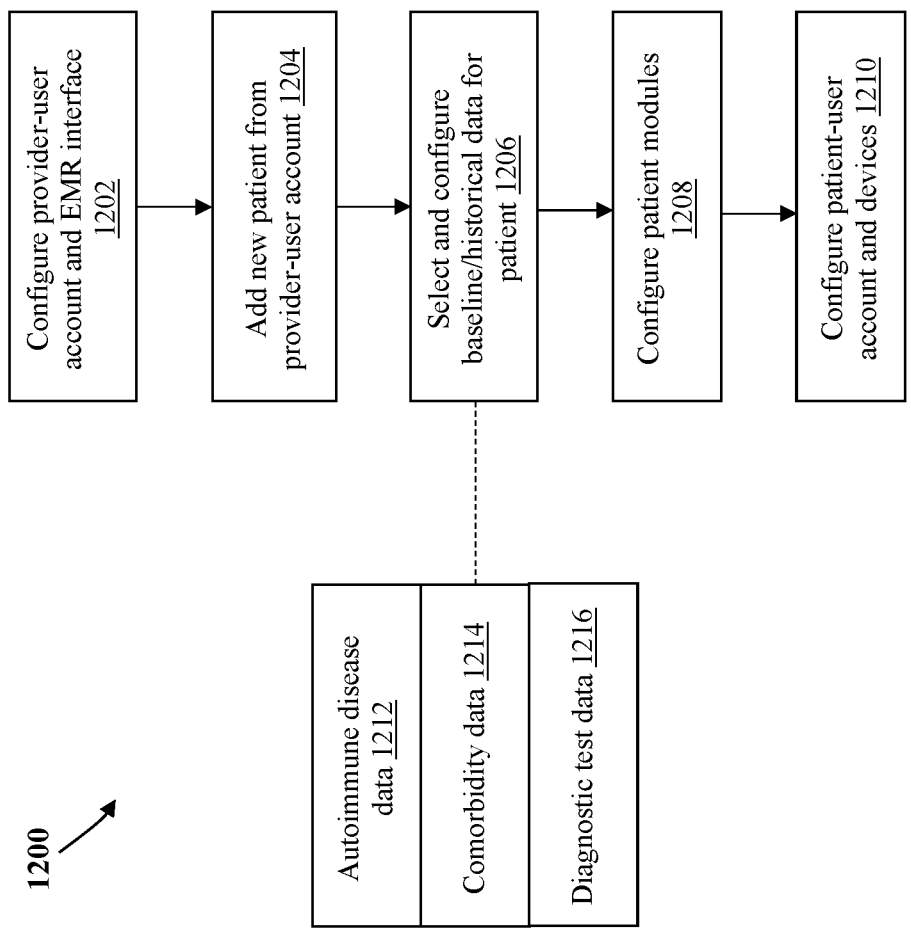
FIG. 12 is a process flow chart of a routine of an auto-immune disease management system, according to certain aspects of the present disclosure.

Referring now to FIG. 12, a process flow diagram of a routine 1200 of an auto-immune disease management system is shown. In accordance with various aspects of the present disclosure, routine 1200 is configured to enable a provider-user (e.g., a medical doctor, or medical personnel, engaged in the clinical treatment of one or more patients suffering from an auto-immune disease or disorder) to configure a provider account for an auto-immune disease management system, configure a communications interface with an electronic medical records (EMR) system and/or other provider business system(s), configure one or more patients profiles within the provider account, and configure one or more patient-users/user devices within the auto-immune disease management system. In accordance with certain embodiments, routine 1200 is initiated by configuring a provider-user account within the auto-immune disease management system and establishing a communications interface with an EMR system 1202. The provider-user may then add one or more patients into the provider-user account 1204, such that the provider user may view and configure one or more system settings associated with the one or more patients. Routine 1200 continues by the provider user selecting a subject patient and selecting and configuring baseline/historical data for the patient 1206. Baseline/historical data may be utilized as part of a training data set in a supervised learning framework and/or may inform one or more rules engine in the recommendation and selection of one or more system modules. Baseline/historical data may comprise autoimmune disease data 1212, such as disease type, disease state, disease activity and disease maturity; comorbidity data 1214, including non-autoimmune related diseases; and/or diagnostic test data 1216, including one or more autoimmune diagnostic test results. The provider-user may then configure one or more patient modules 1208 associated with the subject patient. Routine 1200 may then proceed with configuring a patient-user account for the subject patient, as well as configuring one or more wearable device(s) 1210 being linked to the patient-user account.

Figure 13:
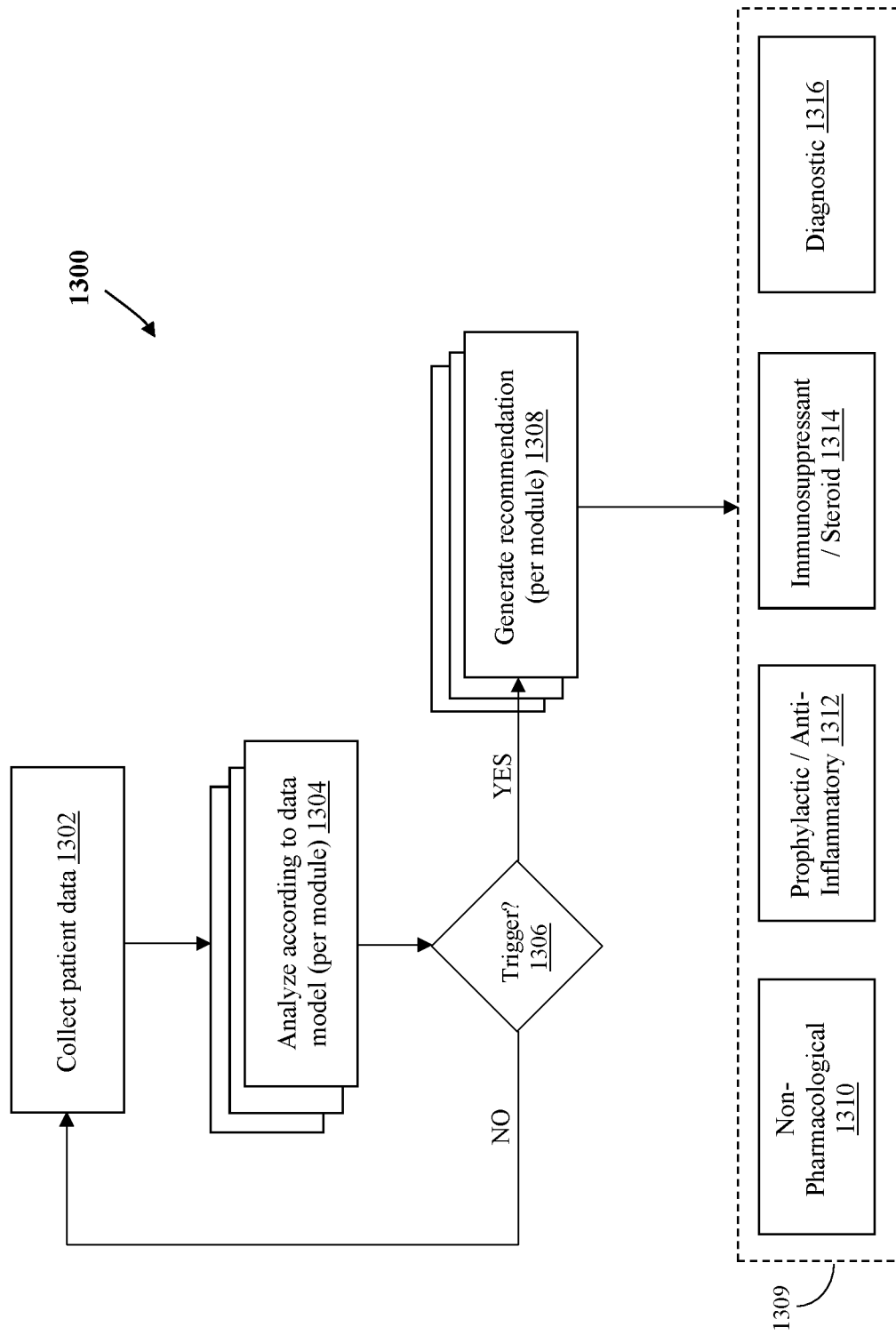
FIG. 13 is a process flow chart of a routine of an auto-immune disease management system, according to certain aspects of the present disclosure.

Referring now to FIG. 13, a process flow diagram of a routine 1300 of an auto-immune disease management system is shown. In accordance with various aspects of the present disclosure, routine 1300 is configured to collect data associated with an autoimmune condition from a patient user via a mobile application and one or more wearable electronic devices, analyze that data according to one or more analytical framework comprising at least one supervised learning model, and generate a recommendation for the diagnosis, management, and/or treatment of a current or future state of the autoimmune condition. In accordance with certain embodiments, routine 1300 is initiated by collecting patient data 1302 via a mobile device, mobile application, and/or wearable electronic device associated with a patient-user account. Routine 1300 proceeds by analyzing the patient data according to one or more data model(s) 1304. In accordance with certain embodiment, routine 1300 may comprise a different data model for each module within the auto-immune disease management system. The one or more data model(s) may be configured to determine the presence of one or more trigger condition 1306 associated with a predicted current or future state of the autoimmune condition. In accordance with certain embodiments, a trigger condition may be assessed/analyzed for each module within the patient application. If a trigger condition is present, routine 1300 proceeds by generating recommendation 1308. If a trigger condition is not present, routine 1300 continues to collect and analyze data from the patient-user. In accordance with certain embodiments, system recommendations 1309 may comprise one or more of a non-pharmacological recommendation 1310, prophylactic/anti-inflammatory recommendation 1312, immunosuppressant/steroid recommendation 1314, and/or a diagnostic recommendation 1316. In accordance with certain embodiments, a non-pharmacological recommendation 1310 may comprise a recommended behavioral modification or activity modification (e.g. a change in diet or reduction of UV exposure). A prophylactic/anti-inflammatory recommendation 1312 may comprise a recommended timing and dosage of a prescription or over-the-counter medication to reduce certain conditions within the patient's body that are known triggers/risk factors for an autoimmune flare (e.g. inflammation). An immunosuppressant/steroid recommendation 1314 may comprise a recommended timing and dosage of a prescription or over-the-counter medication to suppress an undesired immune response. A diagnostic recommendation 1316 may comprise a recommended type and timing for a diagnostic test to screen or diagnose an autoimmune disease or disease state in the patient-user. Routine 1300 may present system recommendations 1309 to the provider-user to aid in the treatment and management of an autoimmune condition in the patient-user.

Figure 14:
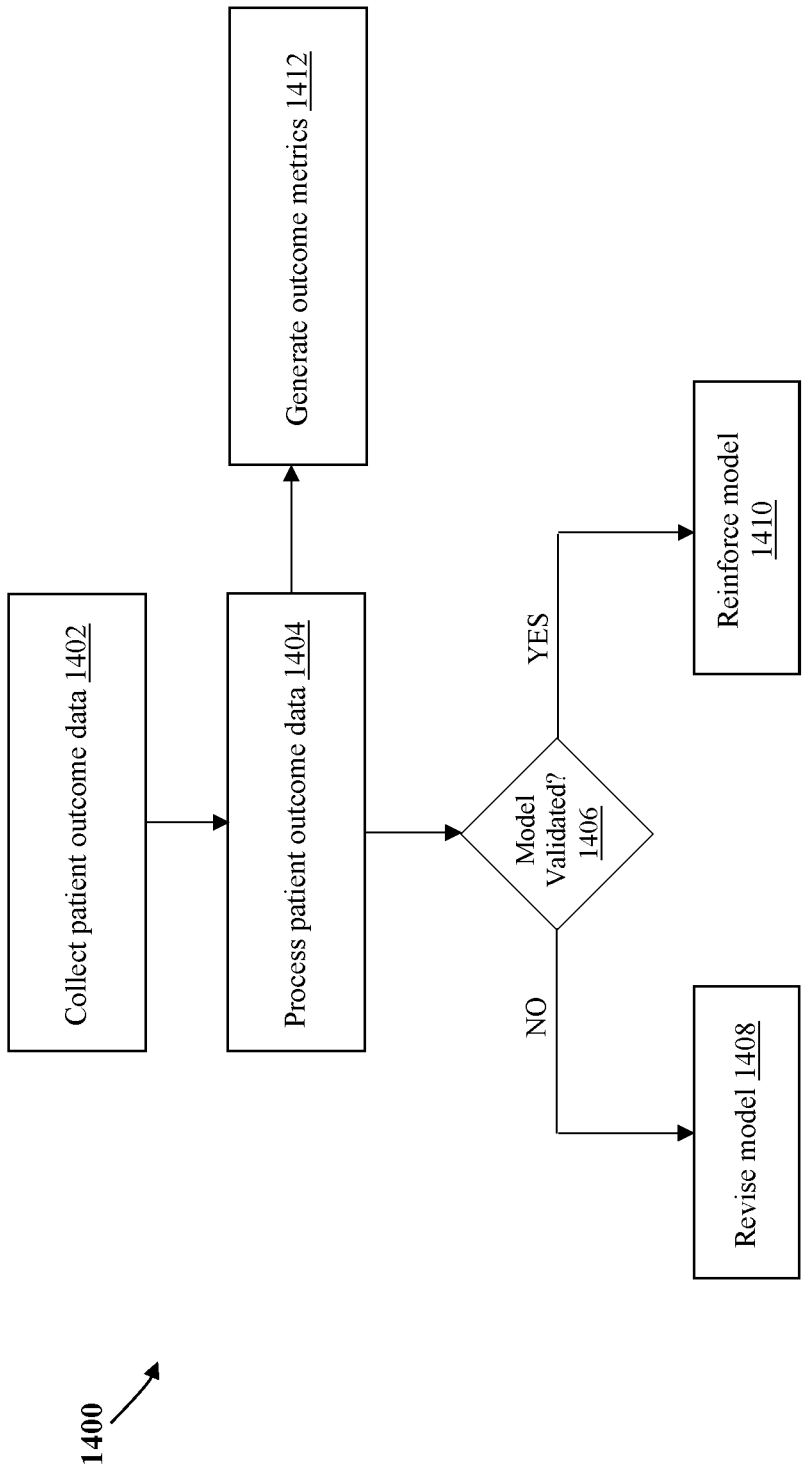
FIG. 14 is a process flow chart of a routine of an auto-immune disease management system, according to certain aspects of the present disclosure.

Referring now to FIG. 14, a process flow diagram of a routine 1400 of an auto-immune disease management system is shown. In accordance with various aspects of the present disclosure, routine 1400 is configured to collect outcome data from a patient-user in response to one or more system recommendation; process the outcome data according to one or more machine learning framework; and generate one or more outcome metrics for a provider-user, a patient-user, and/or a payor-user. In accordance with certain embodiments, routine 1400 is initiated by collecting patient outcome data 1402 from a patient-user, a provider-user, and/or one or more internal or external data sources. Routine 1400 proceeds by processing patient outcome data 1404 according to one or more machine learning framework and/or data model. Routine 1400 proceeds by generating one or more outcome metrics 1412 to assess the progress, improvement, and/or management of the patient's autoimmune condition. Routine 1400 may further comprise a decision step to determine whether the one or more machine learning framework and/or data model is valid/accurate based on the outcome data 1406. If the outcome data does not support the machine learning framework and/or data model, routine 1400 proceeds by revising the model 1408 to more accurately reflect the outcome data. If the outcome data does support the machine learning framework and/or data model, routine 1400 proceeds reinforcing the model 1410 to reinforce one or more causal relationships between a dependent variable and a defined outcome.

Figure 15:
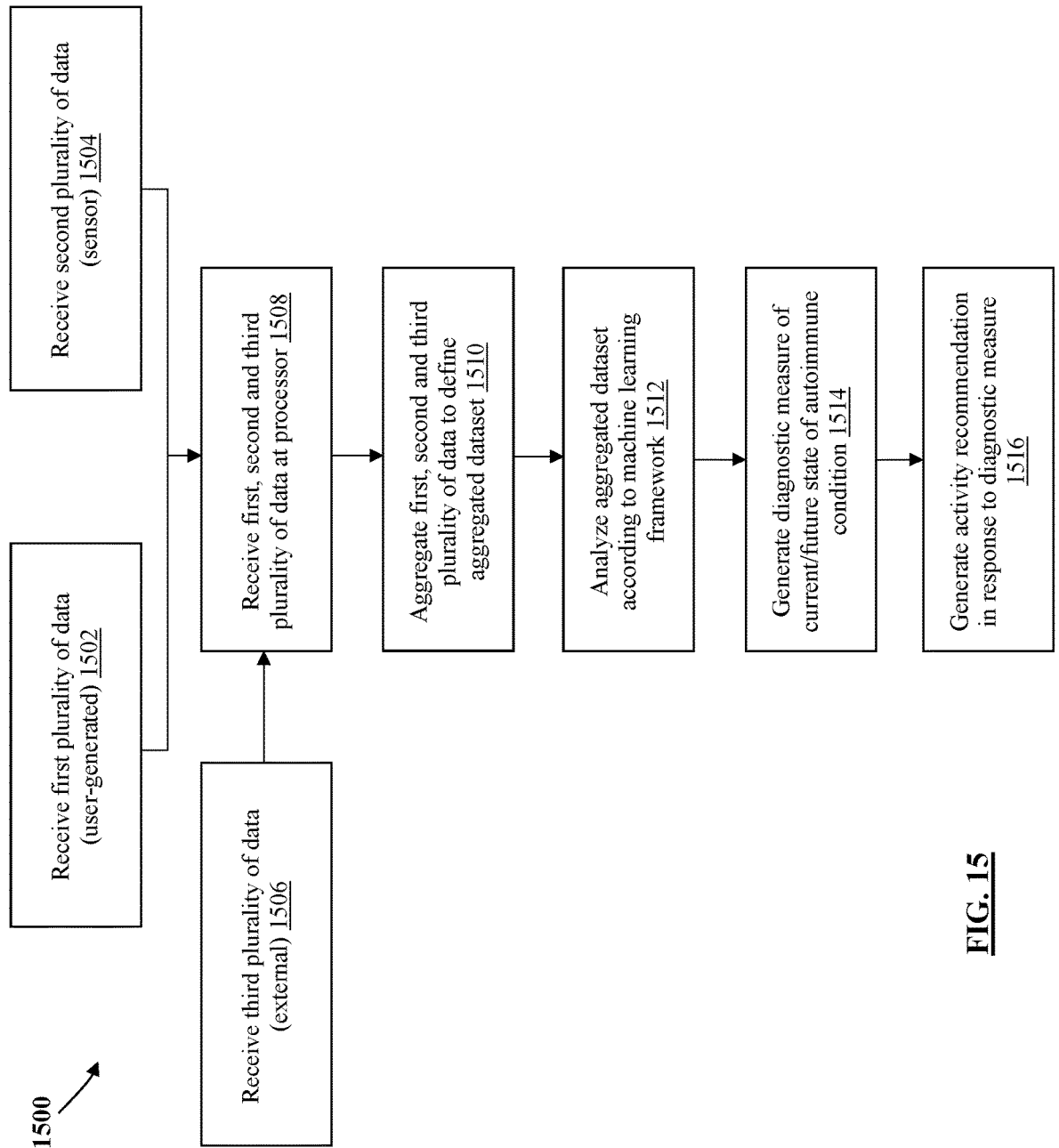
FIG. 15 is a process flow chart of a method for generating a recommendation in response to diagnostic measure, according to embodiments of the invention.

Referring now to FIG. 15, a process flow diagram of a computer-implemented method 1500 for evaluation or management of an autoimmune condition is shown. In accordance with various aspects of the present disclosure, method 1500 comprises receiving, with a mobile electronic device, a first plurality of data comprising one or more user-generated inputs corresponding to an autoimmune condition of a patient user 1502; receiving, with the mobile electronic device, a second plurality of data comprising at least one physiological (sensor) measurement associated with the patient user 1504; and receiving, with a processor, the first plurality of data and the second plurality of data from the mobile electronic device, and a third plurality of data from at least one external data source comprising an electronic medical record system or laboratory information management system 1506. Method 1500 proceeds by aggregating, with the processor, the first plurality of data, the second plurality of data, and the third plurality of data to define an aggregated dataset 1508. The processor is further configured to analyze the aggregated dataset according to at least one machine learning framework comprising at least one supervised learning model or artificial neural network, wherein the at least one machine learning framework comprises at least one dependent variable corresponding to a current or future state of the autoimmune condition 1510. Method 1500 continues by generating, with the processor, at least one diagnostic measure of the current or future state of the autoimmune condition according to the at least one machine learning framework; and generating, with the processor, at least one activity recommendation in response to the at least one diagnostic measure, the at least one activity recommendation corresponding to at least one patient outcome associated with the current or future state of the autoimmune condition.

Figure 16:
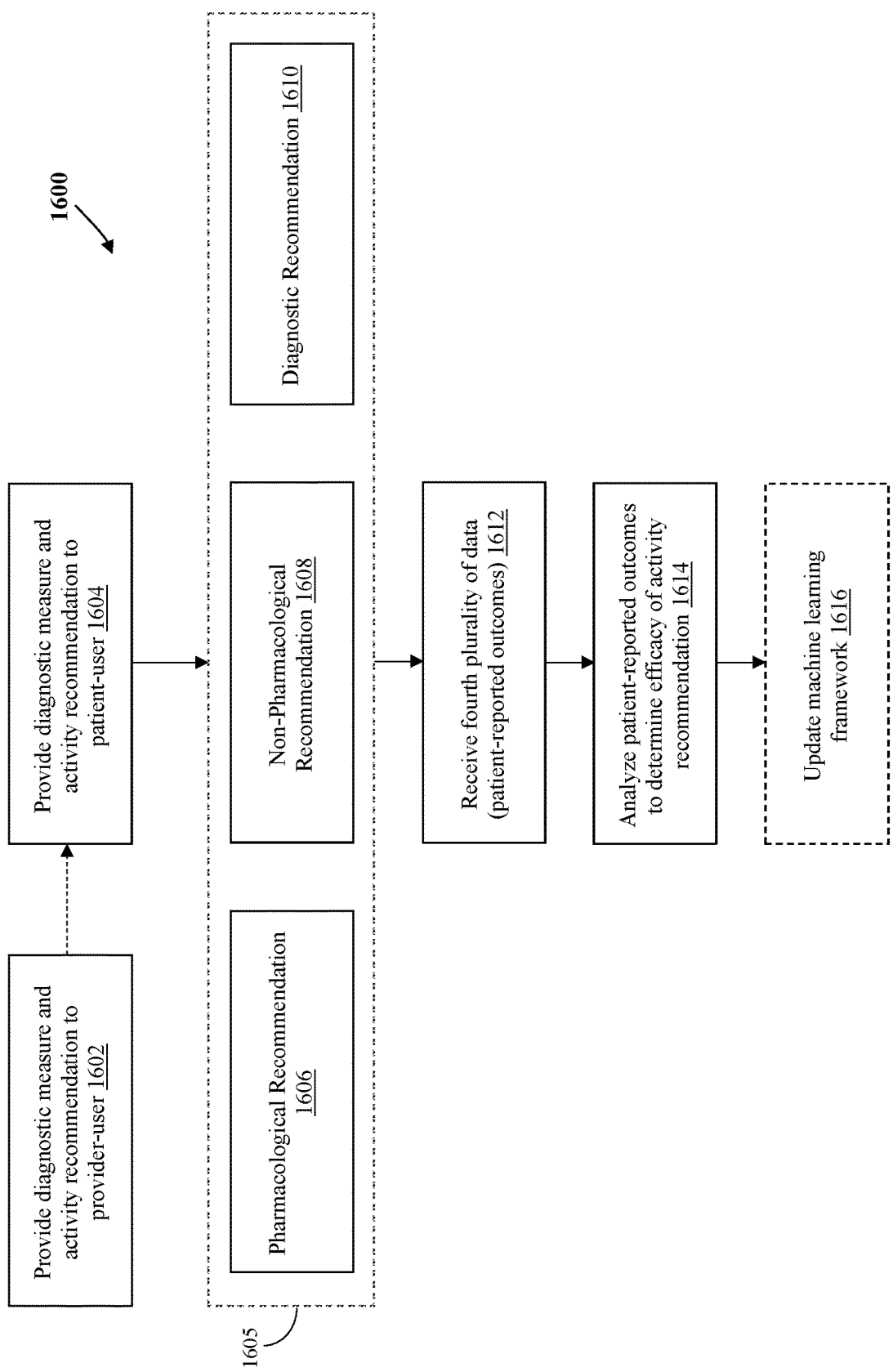
FIG. 16 is a process flow chart of a method for updating a machine learning framework, according to embodiments of the invention.

Referring now to FIG. 16, a process flow diagram of a computer-implemented method 1600 for evaluation or management of an autoimmune condition is shown. In accordance with various aspects of the present disclosure, method 1600 is configured to provide at least one diagnostic measure and activity recommendation to provider-user 1602 in response to analyzing the aggregated dataset according to the at least one machine learning framework (described above). Method 1600 is further configured to provide at least one diagnostic measure and activity recommendation to patient-user 1604. In accordance with certain embodiments, a diagnostic measure and/or activity recommendation 1605 may comprise one or more of a pharmacological recommendation 1606, a non-pharmacological recommendation 1608, and a diagnostic recommendation 1610. In accordance with certain embodiments, a pharmacological recommendation 1606 may comprise a recommended timing and dosage of a prescription or over-the-counter medication to control or mitigate a physiological condition or immune response in the patient user. A non-pharmacological recommendation 1608 may comprise a recommended behavioral modification or activity modification in the patient-user. A diagnostic recommendation 1610 may comprise a recommended type and timing for a diagnostic test to screen or diagnose an autoimmune disease or disease state in the patient-user.

In accordance with certain embodiments, method 1600 may proceed by receiving a fourth plurality of data comprising one or more patient-reported outcomes 1612 in response to the one or more diagnostic measure and/or activity recommendation 1605. Method 1600 may proceed by analyzing the patient-reported outcomes to determine efficacy of the one or more diagnostic measure and/or activity recommendation 1614, and accordingly update the machine learning framework 1616 to improve or reinforce the one or more diagnostic measure and/or activity recommendation.

It will be evident to persons skilled in the art that the above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

Additionally, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

Although embodiments of the invention have been described with a certain degree of particularity, it is understood that the present disclosure is provided by way of example and that various changes to details of construction or arrangement of parts and even steps may be made without departing from the spirit or scope of the invention. The terms and expressions used herein have been employed as terms of description rather than terms of limitation, and their use is not intended as excluding equivalents of the features or steps described thereby.

What is claimed is:

1. A computer-implemented method comprising:
   providing, with at least one application server communicably engaged with a mobile electronic device, a first instance of an end user application to a patient user, wherein the first instance of the end user application comprises a first graphical user interface configured for the patient user, the first graphical user interface comprising one or more interface elements associated with evaluation or management of an autoimmune condition of the patient user;
   providing, with at least one application server communicably engaged with a client device, a second instance of the end user application to a provider user, wherein the second instance of the end user application comprises a second graphical user interface configured for the provider user, the second graphical user interface comprising one or more interface elements associated with the evaluation or management of the autoimmune condition of the patient user;
   receiving, via an input device of the mobile electronic device, a first plurality of data comprising one or more user-generated inputs from the patient user corresponding to the autoimmune condition of the patient user;
   receiving, with at least one wearable electronic device communicably engaged with the mobile electronic device, a second plurality of data comprising at least one physiological measurement from the patient user, wherein the at least one wearable electronic device comprises at least one physiological sensor configured to measure one or more physiological inputs from the patient user when the at least one wearable electronic device is worn by the patient user;
   receiving, with the application server via at least one communications network, the first plurality of data and the second plurality of data from the mobile electronic device, wherein the second plurality of data is communicated to the application server in real-time via at least one communications protocol executed by the first instance of the end user application;
   receiving, with the application server via at least one third-party server communicably engaged with the application server via an application programing interface, a third plurality of data comprising electronic medical record data associated with the patient user;
   aggregating, with a processor of the application server, the first plurality of data, the second plurality of data, and the third plurality of data to define an aggregated dataset;
   analyzing, with an artificial intelligence engine operably engaged with the processor of the application server, the aggregated dataset according to at least one machine learning framework comprising at least one supervised learning model or artificial neural network, wherein the at least one machine learning framework comprises at least one dependent variable corresponding to a current or future state of the autoimmune condition, wherein the at least one machine learning framework is executed by the artificial intelligence engine;
   generating, with the artificial intelligence engine, an output comprising at least one diagnostic measure of the current or future state of the autoimmune condition according to the at least one machine learning framework;
   generating, with the processor of the application server, at least one activity recommendation in response to the at least one diagnostic measure, wherein the at least one activity recommendation corresponds to at least one patient outcome associated with the current or future state of the autoimmune condition;
   providing, with the application server via the at least one communications network, the at least one activity recommendation to the patient user via the first instance of the end user application, wherein the at least one activity recommendation comprises at least one user prompt presented to the patient user via the first graphical user interface of the end user application; and
   providing, with the application server via the at least one communications network, the at least one diagnostic measure and the at least one activity recommendation to the provider user via the second instance of the end user application,
   wherein the second instance of the end user application is configured to receive an input comprising a recommended pharmacological intervention from the provider user via the second graphical user interface in response to providing the at least one diagnostic measure or the at least one activity recommendation and communicate the recommended pharmacological intervention to the patient user at the first instance of the end user application via the at least one communications network.

2. The method of claim 1 further comprising receiving, with the application server via the at least one communications network, a fourth plurality of data from a laboratory information management server via an external application programming interface, wherein the fourth plurality of data comprises laboratory test data associated with the patient user.

3. The method of claim 1 further comprising receiving, with the mobile electronic device, a fourth plurality of data comprising one or more user-generated inputs corresponding to at least one patient-reported outcome in response to the at least one activity recommendation.

4. The method of claim 3 further comprising analyzing, with the processor, the at least one patient-reported outcome to determine a measure of efficacy of the at least one activity recommendation and communicating at least one efficacy data measurement to the practitioner user via the second instance of the end user application.

5. The method of claim 1 wherein the recommended pharmacological intervention comprises a dosage and timing of at least one of a nonsteroidal anti-inflammatory drug, an immunosuppressive drug, and a steroid selected by the provider user.

6. The method of claim 1 wherein the at least one activity recommendation comprises a recommended non-pharmacological intervention comprising a recommended UV exposure mitigation action or recommended activity modification.

7. The method of claim 3 further comprising receiving, with the application server via the at least one communications network, a fourth plurality of data from a third-party weather server via an external application programming interface, wherein the fourth plurality of data comprises UV exposure data for a geographical location associated with the patient user.

8. The method of claim 1 wherein the at least one activity recommendation comprises a recommended laboratory diagnostic procedure comprising an antibody test.

9. The method of claim 1 wherein the mobile electronic device is configured to communicate GPS location data to the application server via at least one communications network.

10. A system comprising:
- a mobile electronic device configured to execute a first instance of an end user application to a patient user, the end user application comprising a graphical user interface comprising a plurality of user prompts associated with an autoimmune condition of the patient user;
- a wearable electronic device communicably engaged with the mobile electronic device, the wearable electronic device comprising at least one physiological sensor configured to collect one or more physiological inputs from the patient user when the wearable electronic device is worn by the patient user;
- an application server communicatively engaged with the mobile electronic device via a communications network, the application server comprising at least one processor; and
- a non-transitory computer readable medium communicably engaged with the at least one processor and having instructions stored thereon that, when executed, cause the at least one processor to perform one or more operations comprising:
  providing the first instance of the end user application to the patient user at the mobile electronic device via the communications network;
  providing a second instance of the end user application to a provider user at a client device via the communications network;
  receiving a plurality of user-generated inputs from the patient user via the first instance of the end user application in response to the plurality of user prompts;
  receiving one or more sensor inputs collected from the wearable electronic device, the one or more sensor inputs comprising a patient activity input or a patient physiological input;
  receiving, from at least one external server via at least one application programming interface, one or more external data inputs comprising at least one patient historical data input;
  aggregating the plurality of user-generated inputs, the one or more sensor inputs, and the one or more external data inputs to define an aggregated dataset;
  analyzing the aggregated dataset according to at least one machine learning framework comprising at least one supervised learning model or artificial neural network, wherein the at least one machine learning framework comprises at least one dependent variable corresponding to a current or future state of the autoimmune condition;
  generating at least one diagnostic measure of the current or future state of the autoimmune condition according to the at least one machine learning framework;
  generating, with the processor, at least one activity recommendation in response to the at least one diagnostic measure, the at least one activity recommendation corresponding to at least one patient action associated with the current or future state of the autoimmune condition;
  providing the at least one activity recommendation to the patient user via the first instance of the end user application;
  providing the at least one diagnostic measure and the at least one activity recommendation to the provider user via the second instance of the end user application;
  receiving a recommended pharmacological intervention from the provider user via the second instance of the end user application in response to providing the at least one diagnostic measure or the at least one activity recommendation; and
  communicating the recommended pharmacological intervention to the patient user at the first instance of the end user application via the communications network.

11. The system of claim 10 wherein the mobile electronic device is configured to communicate GPS location data to the application server via at least one communications network.

12. The system of claim 10 wherein the plurality of user-generated inputs comprises one or more patient-reported outcomes in response to the at least one activity recommendation.

13. The system of claim 10 wherein the one or more external data inputs comprise at least one environmental condition corresponding to a location of the patient user, the at least one environmental condition comprising a UV index.

14. The system of claim 12 wherein the one or more operations further comprise operations for analyzing the aggregated dataset to generate one or more patient outcome metrics associated with the autoimmune condition of the patient user.

15. The system of claim 10 wherein the at least one patient historical data input comprises electronic medical record data or laboratory diagnostic data.

16. The system of claim 10 wherein the one or more operations further comprise operations for providing a communications interface between the mobile electronic device and a provider client device or a health coach client device.

17. The system of claim 14 wherein the one or more operations further comprise operations for communicating the one or more patient outcome metrics to the provider user via the second instance of the end user application.

18. The system of claim 14 wherein the one or more operations further comprise operations for communicating the one or more patient outcome metrics to a payor user via a third instance of the end user application.

19. The system of claim 10 wherein the at least one activity recommendation comprises at least one of a recommended pharmacological intervention, a recommended non-pharmacological intervention, and a laboratory diagnostic procedure.

* * * * *